United States Patent
Shelton, IV et al.

(10) Patent No.: US 11,992,210 B2
(45) Date of Patent: May 28, 2024

(54) MULTIPLE-SENSOR FIRING LOCKOUT MECHANISM FOR POWERED SURGICAL STAPLER

(71) Applicant: Cilag GmbH International, Zug (CH)

(72) Inventors: Frederick E. Shelton, IV, Hillsboro, OH (US); Kevin M. Fiebig, Cincinnati, OH (US); Shane R. Adams, Lebanon, OH (US); Nicholas J. Ross, Franklin, OH (US); Matthew D. Cowperthwait, Cincinnati, OH (US); Curtis A. Maples, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 17/402,701

(22) Filed: Aug. 16, 2021

(65) Prior Publication Data
US 2023/0050358 A1 Feb. 16, 2023

(51) Int. Cl.
*A61B 17/068* (2006.01)
*A61B 17/072* (2006.01)
(Continued)

(52) U.S. Cl.
CPC ........ *A61B 17/0686* (2013.01); *A61B 17/072* (2013.01); *A61B 34/30* (2016.02);
(Continued)

(58) Field of Classification Search
CPC ..... A61B 17/0686; A61B 34/30; A61B 90/98; A61B 17/072; A61B 2017/07257; A61B 2017/07271; A61B 2560/028
See application file for complete search history.

(56) References Cited

U.S. PATENT DOCUMENTS

| 5,129,570 A | 7/1992 | Schulze et al. |
| 7,404,508 B2 | 7/2008 | Smith et al. |

(Continued)

FOREIGN PATENT DOCUMENTS

| EP | 3235444 A2 | 10/2017 |
| EP | 3338657 A1 | 6/2018 |

(Continued)

OTHER PUBLICATIONS

U.S. Appl. No. 17/402,674.
(Continued)

*Primary Examiner* — Andrew M Tecco
*Assistant Examiner* — Nicholas E Igbokwe
(74) *Attorney, Agent, or Firm* — Frost Brown Todd LLP

(57) ABSTRACT

A surgical stapling instrument includes a shaft assembly, an end effector at a distal end of the shaft assembly and having a first jaw with an anvil and a second jaw operable to cooperate with the first jaw to clamp tissue, and a cartridge inserted into the second jaw. The cartridge includes staples, a movable member translatable distally during a firing stroke to discharge the staples into tissue, a first sensor assembly configured to monitor a first condition of the cartridge, and a second sensor assembly configured to monitor a second condition of the cartridge. A first processor is coupled with the first and second sensor assemblies and is configured to receive first and second signals from the sensor assemblies, respectively, where each signal is indicative of the respective condition of the cartridge. The first processor is configured to selectively permit or restrict the firing stroke based upon the signals.

18 Claims, 17 Drawing Sheets

(51) Int. Cl.
*A61B 34/30* (2016.01)
*A61B 90/98* (2016.01)
(52) U.S. Cl.
CPC .... *A61B 90/98* (2016.02); *A61B 2017/07257* (2013.01); *A61B 2017/07271* (2013.01); *A61B 2560/028* (2013.01)

(56) References Cited

U.S. PATENT DOCUMENTS

| | | |
|---|---|---|
| 7,434,715 B2 | 10/2008 | Shelton, IV et al. |
| 7,721,930 B2 | 5/2010 | McKenna et al. |
| 7,810,692 B2 | 10/2010 | Hall et al. |
| 7,832,408 B2 | 11/2010 | Shelton, IV et al. |
| 7,845,537 B2 | 12/2010 | Shelton, IV et al. |
| 8,083,120 B2 | 12/2011 | Shelton, IV et al. |
| 8,210,411 B2 | 7/2012 | Yates et al. |
| 8,408,439 B2 | 4/2013 | Huang et al. |
| 8,453,914 B2 | 6/2013 | Laurent et al. |
| 8,708,213 B2 | 4/2014 | Shelton, IV et al. |
| 9,060,770 B2 | 6/2015 | Shelton, IV et al. |
| 9,186,142 B2 | 11/2015 | Fanelli et al. |
| 9,517,065 B2 | 12/2016 | Simms et al. |
| 9,622,746 B2 | 4/2017 | Simms et al. |
| 9,717,497 B2 | 8/2017 | Zerkle et al. |
| 9,795,379 B2 | 10/2017 | Leimbach et al. |
| 9,808,248 B2 | 11/2017 | Hoffman |
| 9,839,487 B2 | 12/2017 | Dachs, II |
| 10,011,018 B2 | 7/2018 | McGrogan et al. |
| 10,092,292 B2 | 10/2018 | Boudreaux et al. |
| 10,307,170 B2 | 6/2019 | Parfett et al. |
| 10,485,621 B2 | 11/2019 | Morrissette et al. |
| 10,537,400 B2 | 1/2020 | Dachs, II et al. |
| 10,610,313 B2 | 4/2020 | Bailey et al. |
| 10,667,809 B2 | 6/2020 | Bakos et al. |
| 10,806,530 B2 | 10/2020 | Liao et al. |
| 10,863,988 B2 | 12/2020 | Patel et al. |
| 11,020,138 B2 | 6/2021 | Ragosta |
| 11,026,755 B2 | 6/2021 | Weir et al. |
| 11,076,926 B2 | 8/2021 | Ragosta et al. |
| 11,147,552 B2 | 10/2021 | Burbank et al. |
| 11,166,773 B2 | 11/2021 | Ragosta et al. |
| 11,234,700 B2 | 2/2022 | Ragosta et al. |
| 11,259,884 B2 | 3/2022 | Burbank |
| 2006/0185682 A1 | 8/2006 | Marczyk |
| 2011/0006103 A1* | 1/2011 | Laurent ............ A61B 90/30 227/176.1 |
| 2011/0295295 A1* | 12/2011 | Shelton, IV ....... A61B 34/30 606/170 |
| 2012/0209314 A1 | 8/2012 | Weir et al. |
| 2014/0175150 A1* | 6/2014 | Shelton, IV ..... A61B 17/07207 227/176.1 |
| 2015/0272575 A1* | 10/2015 | Leimbach ........... A61B 90/96 227/175.3 |
| 2015/0297228 A1 | 10/2015 | Huitema et al. |
| 2016/0361126 A1 | 12/2016 | Schena et al. |
| 2017/0020617 A1 | 1/2017 | Weir et al. |
| 2017/0265865 A1 | 9/2017 | Burbank |
| 2017/0265954 A1 | 9/2017 | Burbank et al. |
| 2017/0281188 A1* | 10/2017 | Shelton, IV ........ A61B 17/105 |
| 2017/0333037 A1 | 11/2017 | Wellman et al. |
| 2018/0168622 A1* | 6/2018 | Shelton, IV ........ A61B 17/072 |
| 2018/0168756 A1 | 6/2018 | Liao et al. |
| 2018/0271608 A1 | 9/2018 | Ragosta et al. |
| 2018/0310935 A1 | 11/2018 | Wixey |
| 2018/0325606 A1 | 11/2018 | Weir et al. |
| 2018/0344419 A1 | 12/2018 | Dachs, II et al. |
| 2019/0038371 A1 | 2/2019 | Wixey et al. |
| 2019/0076142 A1 | 3/2019 | Wixey |
| 2019/0076143 A1 | 3/2019 | Smith |
| 2019/0167266 A1 | 6/2019 | Patel et al. |
| 2019/0192158 A1* | 6/2019 | Scott ............... A61B 17/2833 |
| 2019/0200989 A1 | 7/2019 | Burbank et al. |
| 2019/0239967 A1 | 8/2019 | Ragosta et al. |
| 2019/0262088 A1 | 8/2019 | Burbank |
| 2020/0093487 A1* | 3/2020 | Baber .............. A61B 90/92 |
| 2020/0138529 A1 | 5/2020 | Ragosta et al. |
| 2020/0397430 A1 | 12/2020 | Patel et al. |
| 2020/0405301 A1 | 12/2020 | Shelton, IV et al. |
| 2021/0393340 A1 | 12/2021 | Beckman et al. |
| 2021/0401433 A1 | 12/2021 | Freidel et al. |

FOREIGN PATENT DOCUMENTS

| | | |
|---|---|---|
| WO | WO 2018/085529 A2 | 5/2008 |
| WO | WO 2015/153642 A1 | 10/2015 |
| WO | WO 2017/083125 A1 | 5/2017 |
| WO | WO 2017/083129 A1 | 5/2017 |
| WO | WO 2018/049198 A1 | 3/2018 |
| WO | WO 2018/049206 A1 | 3/2018 |
| WO | WO 2018/049211 A1 | 3/2018 |
| WO | WO 2018/049217 A1 | 3/2018 |
| WO | WO 2018/052806 A1 | 3/2018 |
| WO | WO 2018/052810 A1 | 3/2018 |
| WO | WO 2018/071497 A1 | 4/2018 |
| WO | WO 2018/071763 A1 | 4/2018 |
| WO | WO 2018/175467 A1 | 9/2018 |
| WO | WO 2019/165403 A1 | 8/2019 |
| WO | WO 2020/131290 A1 | 6/2020 |

OTHER PUBLICATIONS

U.S. Appl. No. 17/402,675.
U.S. Appl. No. 17/402,677.
U.S. Appl. No. 17/402,679.
U.S. Appl. No. 17/402,695.
U.S. Appl. No. 17/402,703.
U.S. Appl. No. 17/402,720.
U.S. Appl. No. 17/402,732.
U.S. Appl. No. 17/402,738.
U.S. Appl. No. 17/402,744.
U.S. Appl. No. 17/402,749; and.
U.S. Appl. No. 17/402,759.
U.S. Appl. No. 17/088,941, entitled "Surgical Stapler End Effector Sled Having Cartridge Wall Support Feature," filed Nov. 4, 2020.
U.S. Appl. No. 17/402,674, entitled "Methods of Operating a Robotic Surgical Stapler," filed Aug. 16, 2021.
U.S. Appl. No. 17/402,675, entitled "Multi-Threshold Motor Control Algorithm for Powered Surgical Stapler," filed Aug. 16, 2021.
U.S. Appl. No. 17/402,677, entitled "Variable Response Motor Control Algorithm for Powered Surgical Stapler," filed Aug. 16, 2021.
U.S. Appl. No. 17/402,679, entitled "Powered Surgical Stapler Having Independently Operable Closure and Firing Systems," filed Aug. 16, 2021.
U.S. Appl. No. 17/402,695, entitled "Firing System Features for Surgical Stapler," filed Aug. 16, 2021.
U.S. Appl. No. 17/402,703, entitled "Proximally Located Firing Lockout Mechanism for Surgical Stapler," filed Aug. 16, 2021.
U.S. Appl. No. 17/402,720, entitled "Cartridge-Based Firing Lockout Mechanism for Surgical Stapler," filed Aug. 16, 2021.
U.S. Appl. No. 17/402,732, entitled "Multi-Position Restraining Member for Sled Movement," filed Aug. 16, 2021.
U.S. Appl. No. 17/402,738, entitled "Firing Member Tracking Feature for Surgical Stapler," filed Aug. 16, 2021.
U.S. Appl. No. 17/402,744, entitled "Adjustable Power Transmission Mechanism for Powered Surgical Stapler," filed Aug. 16, 2021.
U.S. Appl. No. 17/402,749, entitled "Firing Bailout System for Powered Surgical Stapler," filed Aug. 16, 2021.
U.S. Appl. No. 17/402,759, entitled "Deflectable Firing Member for Surgical Stapler," filed Aug. 16, 2021.
International Search Report and Written Opinion dated Dec. 6, 2022 for Application No. PCT/IB2022/057617, 12 pgs.

* cited by examiner

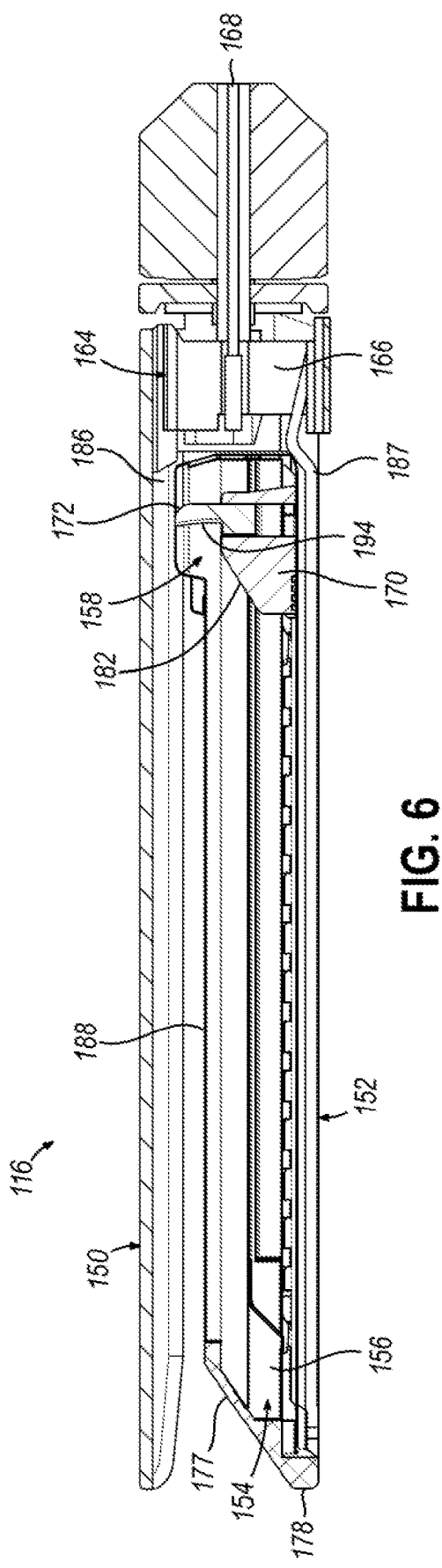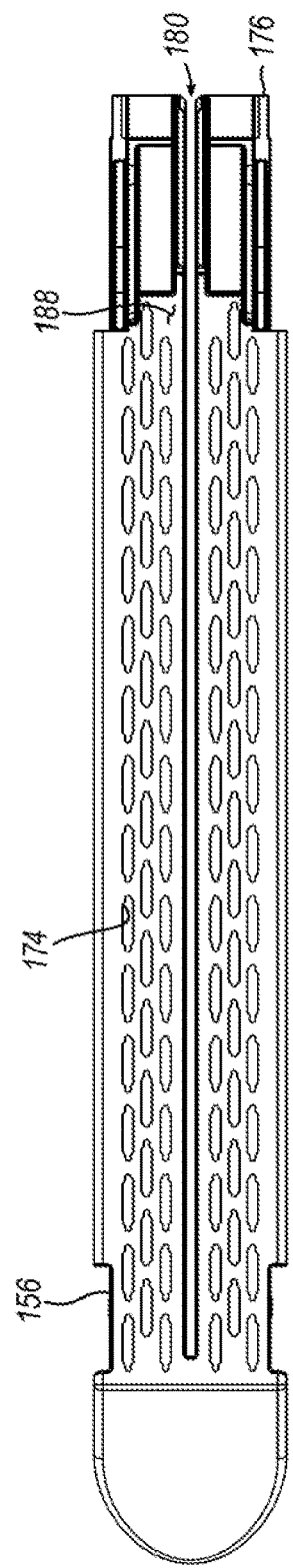

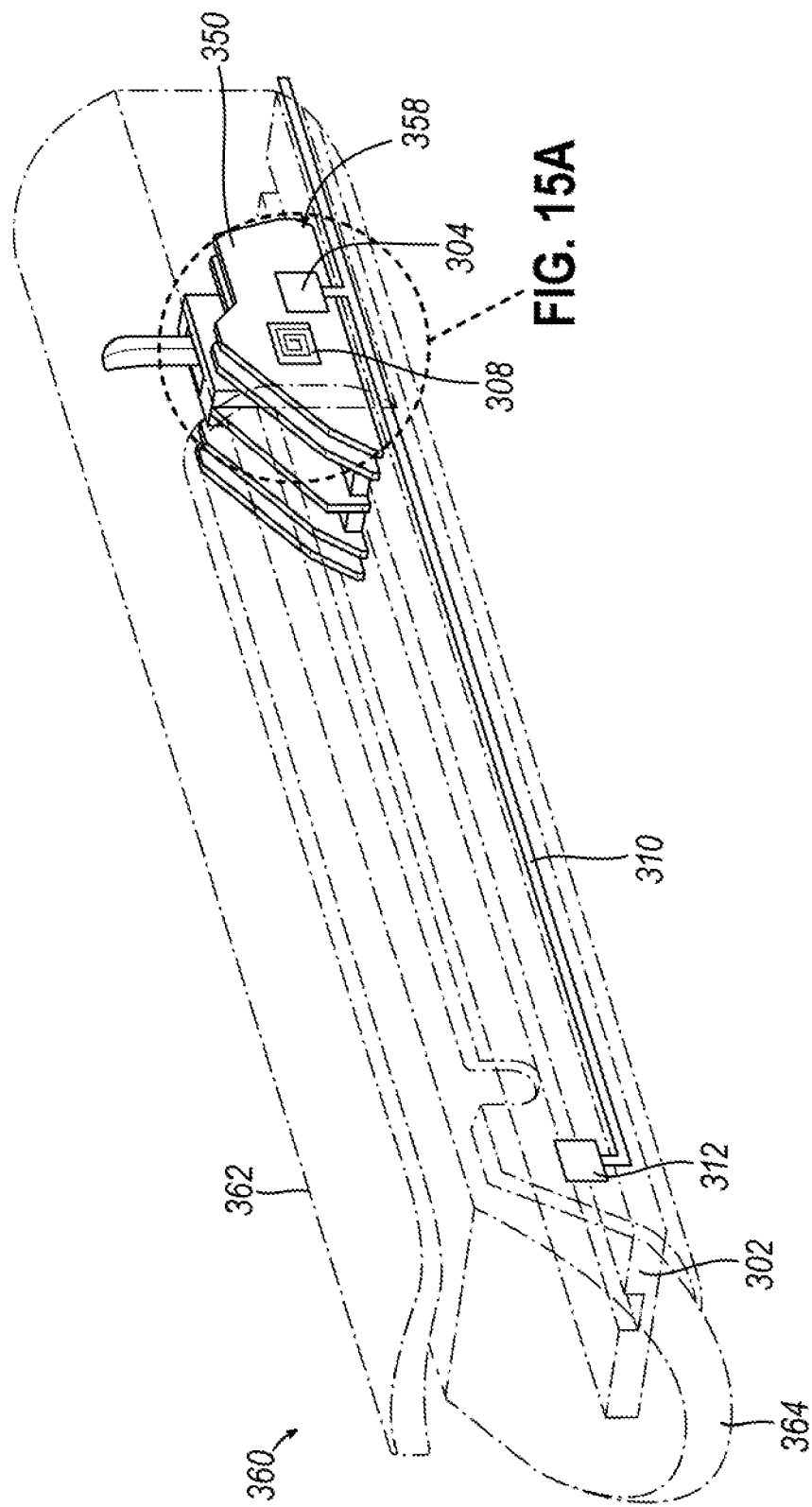

MULTIPLE-SENSOR FIRING LOCKOUT MECHANISM FOR POWERED SURGICAL STAPLER

BACKGROUND

A variety of surgical instruments include an end effector for use in conventional medical treatments and procedures conducted by a medical professional operator, as well as applications in robotically assisted surgeries. Such surgical instruments may be directly gripped and manipulated by a surgeon or incorporated into robotically surgical systems. In the case of robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may include one or more hand input devices (such as joysticks, exoskeletal gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an ultrasonic blade, a surgical stapler, a tissue grasper, a needle driver, an electrosurgical cautery probe, etc. Each of these structures performs functions for the surgeon, for example, cutting tissue, coagulating tissue, holding or driving a needle, grasping a blood vessel, dissecting tissue, or cauterizing tissue.

Examples of surgical instruments include surgical staplers. Some such staplers are operable to clamp down on layers of tissue, cut through the clamped layers of tissue, and drive staples through the layers of tissue to substantially seal the severed layers of tissue together near the severed ends of the tissue layers. Examples of surgical staplers and associated features are disclosed in U.S. Pat. No. 7,404,508, entitled "Surgical Stapling and Cutting Device," issued Jul. 29, 2008; U.S. Pat. No. 7,434,715, entitled "Surgical Stapling Instrument Having Multistroke Firing with Opening Lockout," issued Oct. 14, 2008; U.S. Pat. No. 7,721,930, entitled "Disposable Cartridge with Adhesive for Use with a Stapling Device," issued May 25, 2010; U.S. Pat. No. 8,408,439, entitled "Surgical Stapling Instrument with An Articulatable End Effector," issued Apr. 2, 2013; U.S. Pat. No. 8,453,914, entitled "Motor-Driven Surgical Cutting Instrument with Electric Actuator Directional Control Assembly," issued Jun. 4, 2013; U.S. Pat. No. 9,186,142, entitled "Surgical Instrument End Effector Articulation Drive with Pinion and Opposing Racks," issued on Nov. 17, 2015; U.S. Pat. No. 9,795,379, entitled "Surgical Instrument with Multi-Diameter Shaft," issued Oct. 24, 2017; U.S. Pat. No. 9,808,248, entitled "Installation Features for Surgical Instrument End Effector Cartridge," issued Nov. 7, 2017; U.S. Pat. No. 10,092,292, entitled "Staple Forming Features for Surgical Stapling Instrument," issued Oct. 9, 2018; U.S. Pat. No. 9,717,497, entitled "Lockout Feature for Movable Cutting Member of Surgical Instrument," issued Aug. 1, 2017; U.S. Pat. No. 9,517,065, entitled "Integrated Tissue Positioning and Jaw Alignment Features for Surgical Stapler," issued Dec. 13, 2016; U.S. Pat. No. 9,622,746, entitled "Distal Tip Features for End Effector of Surgical Instrument," issued Apr. 18, 2017; and U.S. Pat. No. 8,210,411, entitled "Motor-Driven Surgical Instrument," issued Jul. 3, 2012. The disclosure of each of the above-cited U.S. Patents is incorporated by reference herein in its entirety.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 6 depicts a side cross-sectional view of the end effector of FIG. 4, where the end effector includes a staple cartridge;

FIG. 7 depicts a top view of a deck of the staple cartridge of FIG. 6;

FIG. 14 depicts a perspective view of the end effector of FIG. 13 with portions thereof shown in broken lines to reveal internal features, showing a wedge sled in a proximal, un-fired position;

Figure 1:
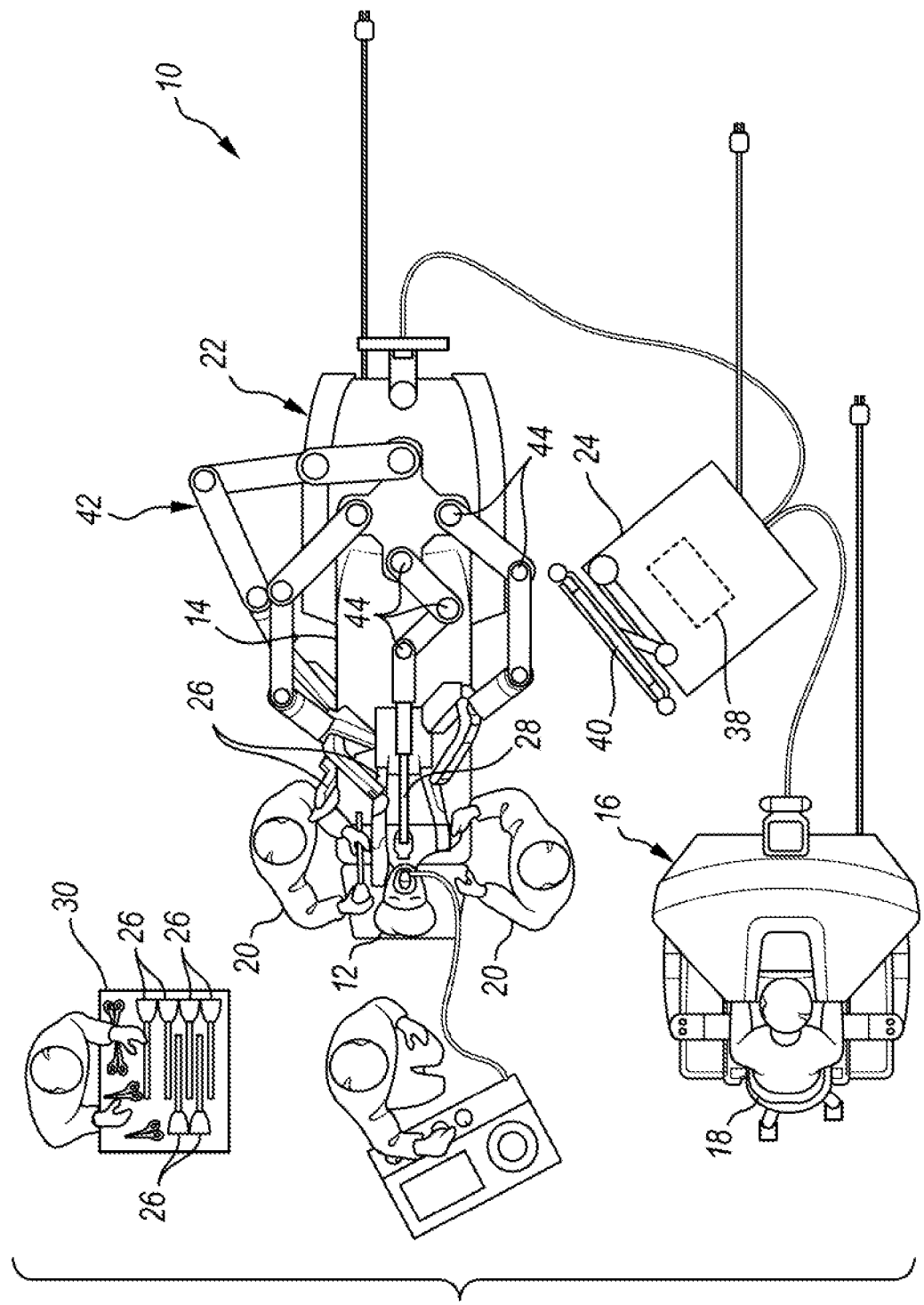
FIG. 1 depicts a top plan view of a robotic surgical system being used to perform a surgical procedure.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "clockwise," "counterclockwise," "inner," "outer," "upper," "lower," and the like also are used herein for reference to relative positions and directions. Such terms are used below with reference to views as illustrated for clarity and are not intended to limit the invention described herein.

Aspects of the present examples described herein may be integrated into a robotically-enabled medical system, including as a robotic surgical system, capable of performing a variety of medical procedures, including both minimally invasive, such as laparoscopy, and non-invasive, such as endoscopy, procedures. Among endoscopy procedures, the robotically-enabled medical system may be capable of performing bronchoscopy, ureteroscopy, gastroscopy, etc.

I. Exemplary Robotic Surgical System

A. Overview

FIG. 1 shows a top plan view of an exemplary robotic surgical system (10) that may be used for performing a diagnostic or surgical procedure on a patient (12) who is lying down on an operating table (14). Robotic surgical system (10) may be constructed and operable in accordance with at least some of the teachings of U.S. Pat. No. 9,839,487, entitled "Backup Latch Release for Surgical Instrument," issued Dec. 12, 2017; U.S. Pat. No. 10,485,621, entitled "Sterile Barrier Between Surgical Instrument and Teleoperated Actuator," issued Nov. 26, 2019; U.S. Pat. No. 10,806,530, entitled "System and Method for Patient-Side Instrument Control," issued Oct. 20, 2020; U.S. Pat. No. 10,537,400, entitled "Detection Pins to Determine Presence of Surgical Instrument and Adapter on Manipulator," issued Jan. 21, 2020; U.S. Pat. No. 10,863,988, entitled "Surgical Instrument with Lockout Mechanism," published Dec. 15, 2020; U.S. Pat. No. 10,610,313, entitled "Surgical Instrument with Shiftable Transmission," issued Apr. 7, 2020; U.S. Pub. No. 2018/0271608, entitled "Manual Release for Medical Device Drive System," published Sep. 27, 2018; U.S. Pub. No. 2018/0325606, entitled "Systems and Methods for Operating an End Effector," published Nov. 15, 2018; U.S. Pub. No. 2019/0200989, entitled "Stapler Reload Detection and Identification," published Jul. 4, 2019; U.S. Pub. No. 2019/0239967, entitled "Stapler Beam Architecture," published Aug. 8, 2019; U.S. Pub. No. 2019/0262088, entitled "Robotic Surgical Stapler Assembly Configured to Use Stapler Reload," published Aug. 29, 2019; U.S. Pub. No. 2019/0239877, entitled "Wrist Architecture," published Aug. 8, 2019; U.S. Pub. No. 2019/0201150, entitled "Push-Pull Surgical Instrument End Effector Actuation Using Flexible Tension Member," published Jul. 4, 2019; U.S. Pub. No. 2019/0282233, entitled "Stapler Cartridge With an Integral Knife," published Sep. 19, 2019; U.S. Pub. No. 2019/0262088, entitled "Robotic Surgical Stapler Assembly Configured to Use Stapler Reload," published Aug. 29, 2019; U.S. Pub. No. 2020/0138529, entitled "Locking System for Medical Device Drive System," published May 7, 2020; and/or U.S. Pub. No. 2020/0397430, entitled "Surgical Instrument With Lockout Mechanism," published Dec. 24, 2020. The disclosure of each of the above-cited U.S. Patents and U.S. Patent Publications is incorporated by reference herein in its entirety.

Robotic surgical system (10) may include a surgeon's console (16) for use by a surgeon (18) during a surgical procedure. One or more assistants (20) may also participate in the procedure. Robotic surgical system (10) may include a patient side cart (22) (i.e., a surgical robot) and an electronics cart (24). Patient side cart (22) may manipulate at least one surgical instrument (26) (also referred to as a "tool assembly" or "tool") through an incision in the body of patient (12) while surgeon (18) views the surgical site through surgeon's console (16). As will be described in greater detail below, surgical instrument(s) (26) and an imaging device (shown as an endoscope (28)) may be removably coupled with patient side cart (22). Electronics cart (24) may be used to process the images of the surgical site for subsequent display to the surgeon (18) through surgeon's console (16). Electronics cart (24) may be coupled with endoscope (28) and may include a processor (38) (shown schematically) to process captured images for subsequent display, such as to surgeon (18) on the surgeon's console (16), on a display (40) of electronics cart (24), or another suitable display located locally and/or remotely. The images may also be processed by a combination of electronics cart (24) and processor (38), which may be coupled together to process the captured images jointly, sequentially, and/or combinations thereof. Electronics cart (24) may overlay the captured images with a virtual control interface prior to displaying combined images to the surgeon (18) via surgeon's console (16).

Figure 2:
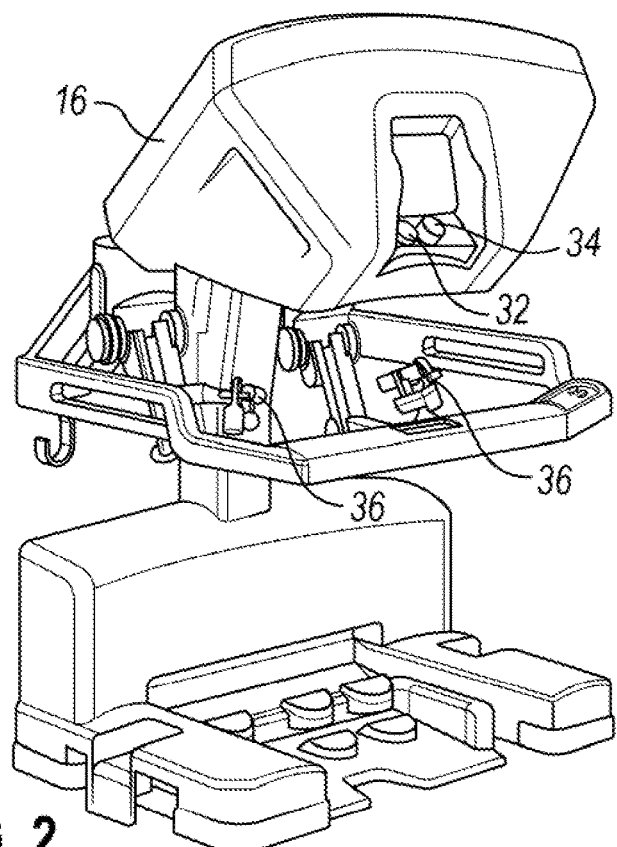
FIG. 2 depicts a perspective view of a surgeon's control console of the robotic surgical system of FIG. 1.

FIG. 2 shows a perspective view of surgeon's console (16). Surgeon's console (16) includes a left eye display (32) and a right eye display (34) for presenting surgeon (18) with a coordinated stereo view of the surgical site that enables depth perception. Surgeon's console (16) includes one or more input control devices (36) causing patient side cart (22) (shown in FIG. 1) to manipulate one or more surgical instruments (26). Input control devices (36) may provide the same degrees of freedom as their associated surgical instruments (26) (shown in FIG. 1) to provide surgeon (18) with telepresence, or the perception that the input control devices (36) are integral with surgical instruments (26). To this end, position, force, and tactile feedback sensors (not shown) may be employed to transmit position, force, and tactile sensations from surgical instruments (26) back to the surgeon's hands through input control devices (36). In some instances, surgeon's console (16) may be located in the same room as the patient so that surgeon (18) may directly monitor the procedure, be physically present if necessary, and speak to an assistant directly rather than over the telephone or other communication medium. Alternatively, surgeon (18) may be located in a different room, a completely different building, or other remote location from the patient allowing for remote surgical procedures.

Figure 3:
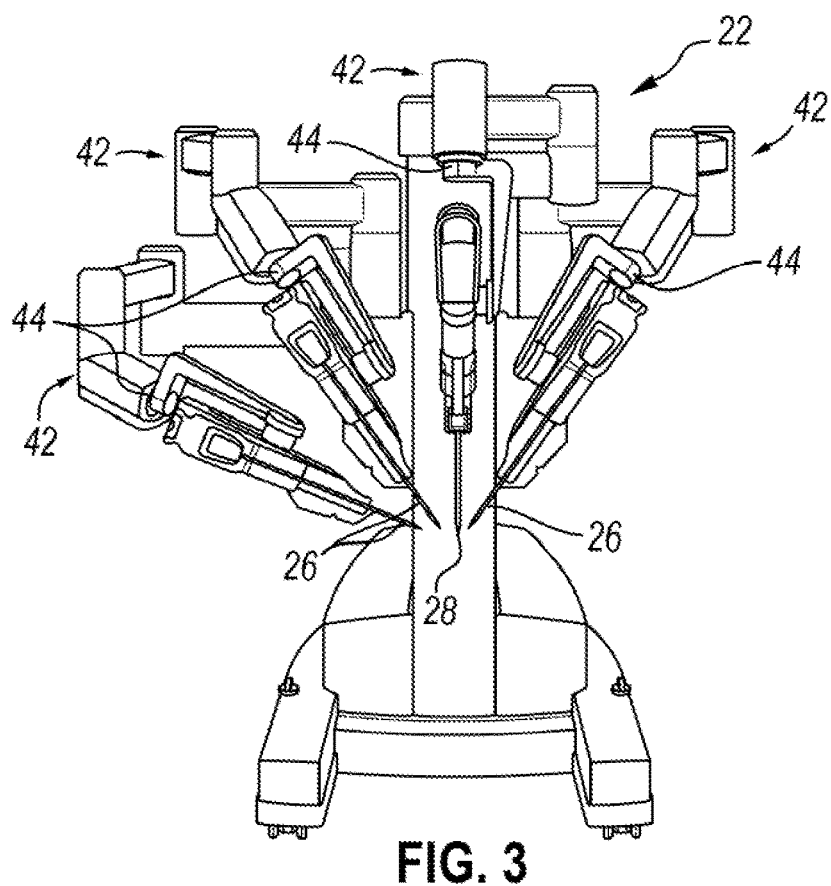
FIG. 3 depicts a front elevation view of a patient side cart of the robotic surgical system of FIG. 1.

FIG. 3 shows patient side cart (22) that manipulates surgical instruments (26). An image of the surgical site may be obtained by endoscope (28), which may include a stereoscopic endoscope. Manipulation is provided by robotic mechanisms, shown as robotic arms (42) that include at least one robotic joint (44) and an output coupler (not shown) that is configured to removable secure surgical instrument (26) with robotic arm (42). Endoscope (28) and surgical tools (26) may be positioned and manipulated through incisions in the patient so that a kinematic remote center is maintained at the incision to minimize the size of the incision. Images of the surgical site may include images of the distal ends of the surgical instruments (26) when they are positioned within the field-of-view of the endoscope (28). Patient side cart (22) may output the captured images for processing outside electronics cart (24). The number of surgical instruments (26) used at one time will generally depend on the diagnostic or surgical procedure and the space constraints within the operating room, among other factors. To change one or more of surgical instruments (26) being used during a procedure, assistant(s) (20) may remove surgical instrument (26) from patient side cart (22) and replace surgical instrument (26) with another surgical instrument (26) from a tray (30) (shown in FIG. 1) in the operating room.

B. Exemplary Surgical Instrument

Figure 4:
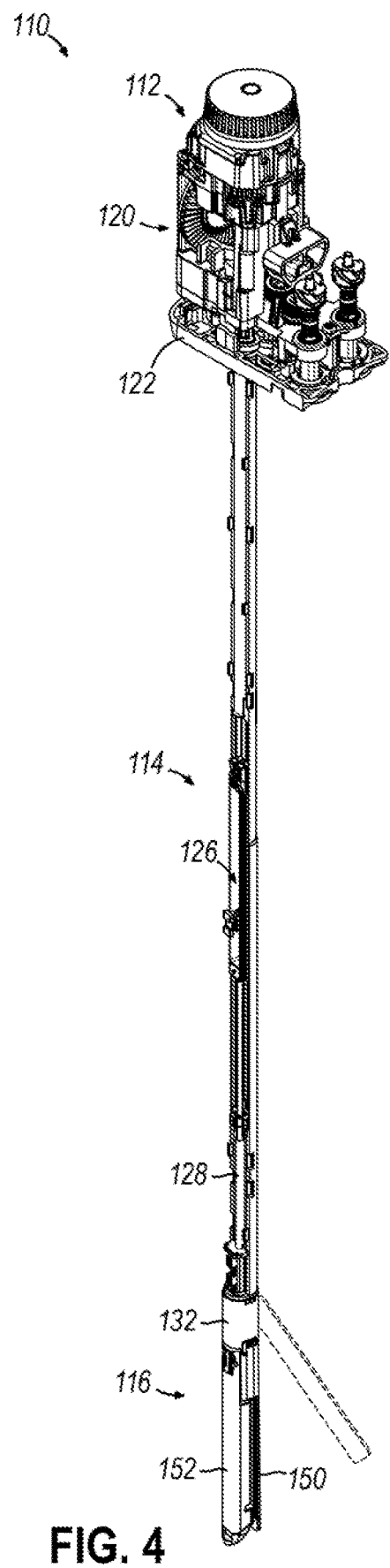
FIG. 4 depicts a perspective view of an exemplary surgical instrument that may be used with the robotic surgical system of FIG. 1, where the surgical instrument includes an instrument base, an elongate shaft, and an end effector, with select portions of the surgical instrument omitted to reveal internal features.
Figure 5:
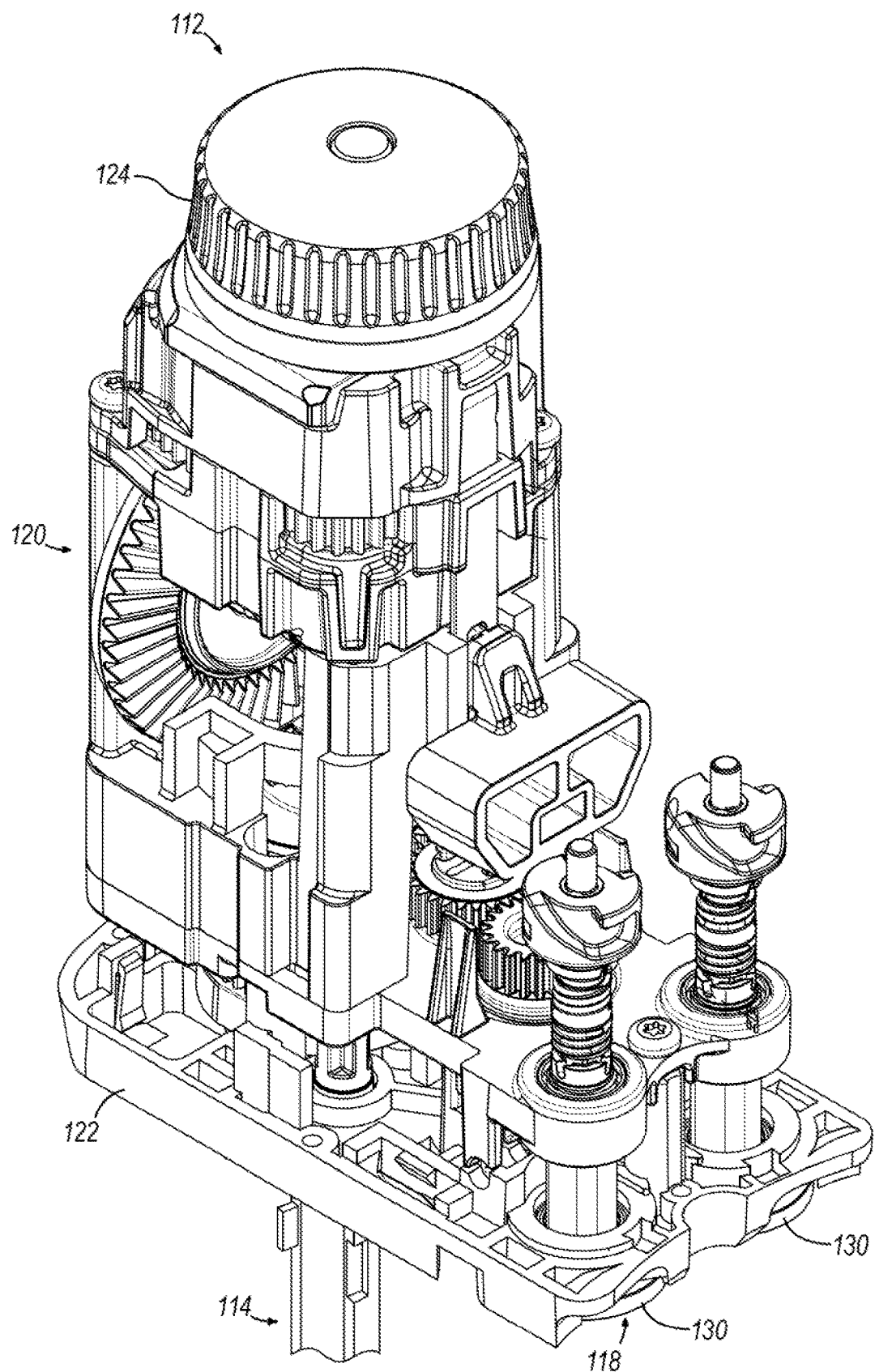
FIG. 5 depicts an enlarged perspective view of the instrument base of the surgical instrument of FIG. 4, with an outer housing omitted to reveal internal features.

FIGS. 4-5 show an exemplary surgical instrument (110) that may be mounted on and used with patient side cart (22) shown in FIG. 3. Surgical instrument (110) can have any of a variety of configurations capable of performing one or more surgical functions. As shown, surgical instrument (110) includes an instrument base (112), a shaft assembly (114) extending distally from instrument base (112), and an end effector (116) at a distal end of shaft assembly (114). Instrument base (112) includes an attachment interface (118) that includes input couplers (130) that are configured to interface with and be driven by corresponding output couplers (not shown) of robotic arm (42) of patient side cart (22).

FIG. 5 shows an enlarged perspective view of instrument base (112) of surgical instrument (110). Instrument base (112) includes a drive system (120) mounted on a chassis (122) and having one or more actuators for actuating end effector (116) to clamp, staple, and cut tissue, and for articulating end effector (116) relative to a longitudinal axis defined by shaft assembly (114). Drive system (120) may include a manual actuator (124), which is shown in the form of a knob configured to be manually rotated. Manual actuator (124) may engage other components of surgical instrument (110) to serve as a "bailout" mechanism to obtain a desired movement in end effector (116) without powered actuation of drive system (120). Shaft assembly (114) may include additional drive components, such as portions of a drive train (126), that may couple instrument base (112) to a moveable feature (128) of shaft assembly (114) that may be coupled to end effector (116). Shaft assembly (114) may be configured for use with a variety of interchangeable end effectors (116), such as a cutter, grasper, a cautery tool, a camera, a light, or a surgical stapler, for example.

C. First Exemplary End Effector

FIG. 6 shows a cross-sectional side view of end effector (116) of surgical instrument (110). End effector (116) extends distally from a distal end of shaft assembly (114). In the present example, end effector (116) comprises a surgical stapler, which may also be referred to herein as an "endocutter," configured to clamp, cut, and staple tissue. As illustrated, end effector (116) includes opposing upper and lower jaws (150, 152) configured to move relative to one another between open and closed positions for clamping and releasing tissue.

One or both of upper and lower jaws (150, 152) may be configured to pivot and thereby actuate end effector (116) between open and closed positions. Lower jaw (152) includes a staple cartridge tray (177) which accepts a removable staple cartridge (154) therein. In the illustrated example, lower jaw (152) is pivotable relative to upper jaw (150) to move between an open, unclamped position and a closed, clamped position. In other examples, upper jaw (150) may move relative to lower jaw (152) (e.g., similar to end effector (210) of FIGS. 9-10). In still other examples, both and upper and lower jaws (150, 152) may move to actuate end effector (116) between open and closed positions. In the present example, lower jaw (152) is referred to as a "cartridge jaw" or "channel jaw," and upper jaw (150) is referred to as an "anvil jaw."

Figure 8:
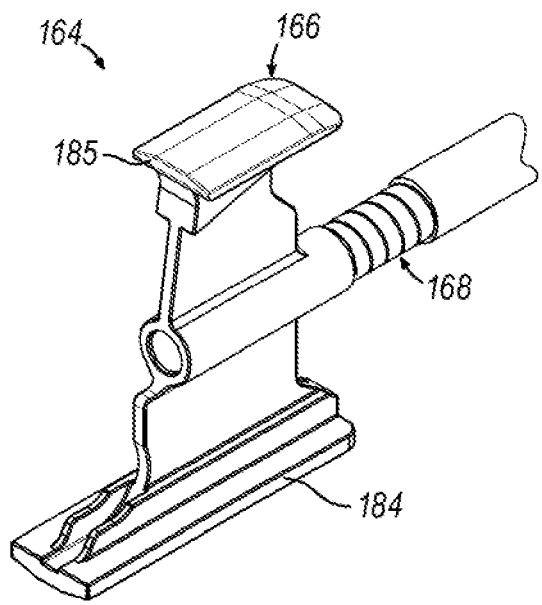
FIG. 8 depicts a driving assembly configured for use with the staple cartridge of FIG. 7.
Figure 9:
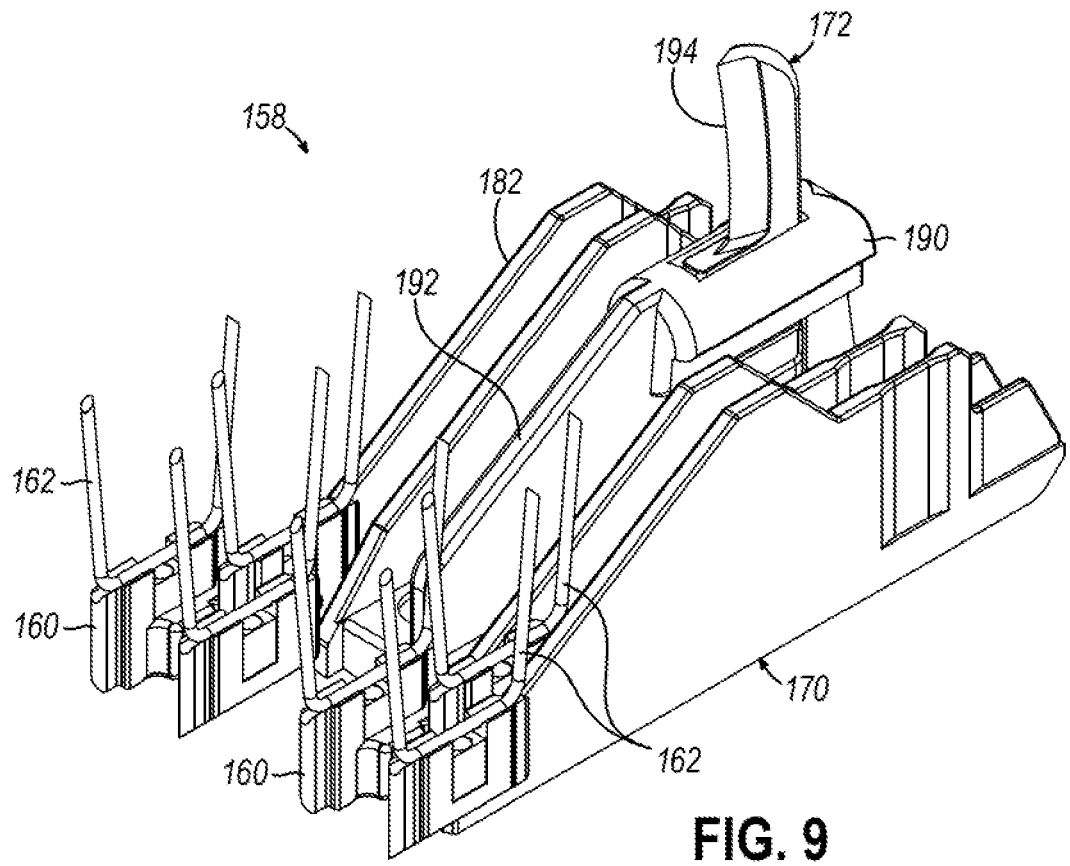
FIG. 9 depicts a firing assembly, staple drivers, and staples configured for use with the staple cartridge of FIG. 7.

Upper jaw (150) defines a surface that has a plurality of pockets (not shown) and operates as an anvil to deform staples ejected from staple cartridge (154) during operation. Staple cartridge (154) is replaceable, for example, by removing a used staple cartridge (154) from end effector (116) and inserting a new staple cartridge (154) into lower jaw (152). Staple cartridge (154) includes a staple cartridge body (156) that houses a firing assembly (158), a plurality of staple drivers (160) (also referred to as staple pushers), and a plurality of staples (162). As shown in FIGS. 6 and 8, end effector (116) includes a driving assembly (164) that includes a pusher member (166) that is operatively coupled with an actuation mechanism via a push rod (168). As shown in FIG. 6 and FIG. 9, firing assembly (158) includes a wedge sled (170) (also referred to as a staple pushing shuttle), and a knife member (172).

FIG. 7 shows a top view of staple cartridge body (156). Staple cartridge body (156) includes an array of staple accommodating apertures (174) (also known as openings) extending through an upper deck (188) of staple cartridge body (156). Each aperture (174) slidably houses a respective staple (162) in an unformed state and a free end of a corresponding staple driver (160) positioned beneath the unformed staple (162). Staple cartridge (154) includes proximal and distal ends (176, 178). In operation, staples (162) are sequentially deployed from apertures (174) by staple drivers (160) starting at proximal end (176) and advancing toward distal end (178). A vertical slot (180), configured to accommodate knife member (172), extends through part of staple cartridge (154).

FIG. 8 shows pusher member (166) as including first and second flanges (184, 185). First flange (184) is configured to be received in a longitudinal slot (186) (shown in FIG. 6) of upper jaw (150) and second flange (185) is configured to be received in a longitudinal slot (187) (shown in FIG. 6) of staple cartridge body (156) of lower jaw (152). First and second flanges (184, 185) move along longitudinal slots (186, 187) during actuation of pusher member (166). In some versions, pusher member (166) may include a single flange (e.g., omitting first flange (184)). As shown, longitudinal slot (186) is generally enclosed and longitudinal slot (187) opens to an exterior surface of lower jaw (152).

FIG. 9 shows a perspective view of firing assembly (158), which is configured to be slidably received within the proximal end of staple cartridge body (156) in a longitudinal direction prior to engaging staple drivers (160) and staples (162). Wedge sled (170) of firing assembly (158) slidingly interfaces with staple cartridge body (156). More specifically, wedge sled (170) advances distally along staple cartridge body (156) such that ramp portions (182) of wedge sled contact staple drivers (160). Staple drivers (160) push staples (162) out of apertures (174) of staple cartridge body (156) to penetrate through and staple tissue clamped between staple cartridge body (156) and upper jaw (150). An initial distal actuation of pusher member (166) may move pusher member (166) into contact with wedge sled (170), with further actuation pushing staples (162) transversely out of staple cartridge body (156).

At an initial proximal position of wedge sled (170), knife member (172) is housed within staple cartridge body (156). The position of knife member (172) is controlled during a first portion of the movement of wedge sled (170) from proximal end (176) of staple cartridge body (156) to distal end (178) of staple cartridge (154), so that a cutting edge (194) of knife member (172) extends through vertical slot (180). Vertical slot (180) accommodates cutting edge (194) of knife member (172) as firing assembly (158) is moved toward distal end (178) of staple cartridge (154). Wedge sled (170) includes a guide member (190) that provides a bearing surface that cooperates with a similarly shaped surface of staple cartridge body (156) to guide wedge sled (170). Guide member (190) extends from a vertical rib member (192) of wedge sled (170), which forms a central portion of wedge sled (170). In some versions, knife member (172), or at least cutting edge (194), may be retracted below upper deck (188) of staple cartridge body (156) prior to firing assembly (158) reaching its distal most position adjacent to distal end (178) of staple cartridge (154).

D. Second Exemplary End Effector

Figure 10:
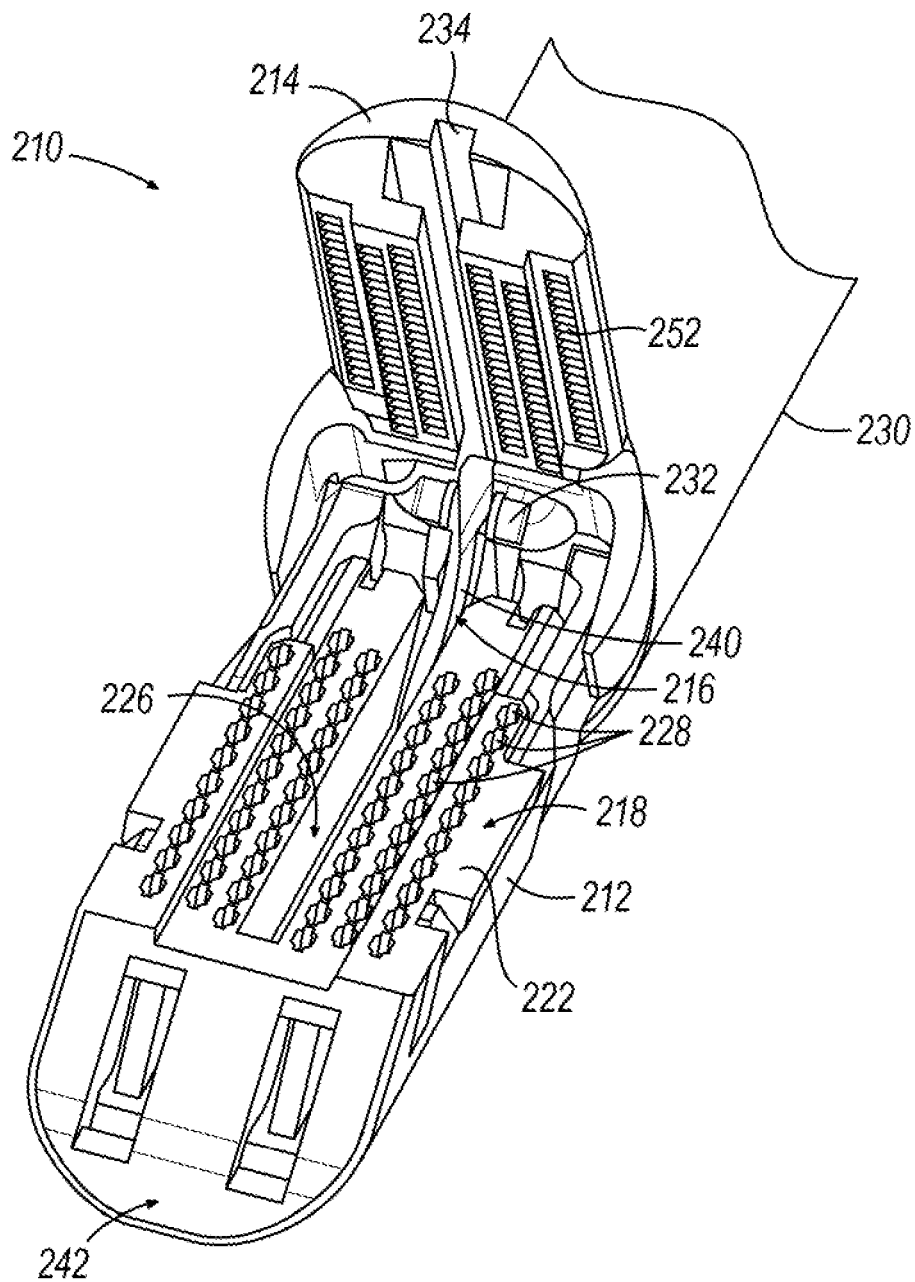
FIG. 10 depicts a second exemplary end effector that may be configured for use with the robotic surgical system of FIG. 1.
Figure 11:
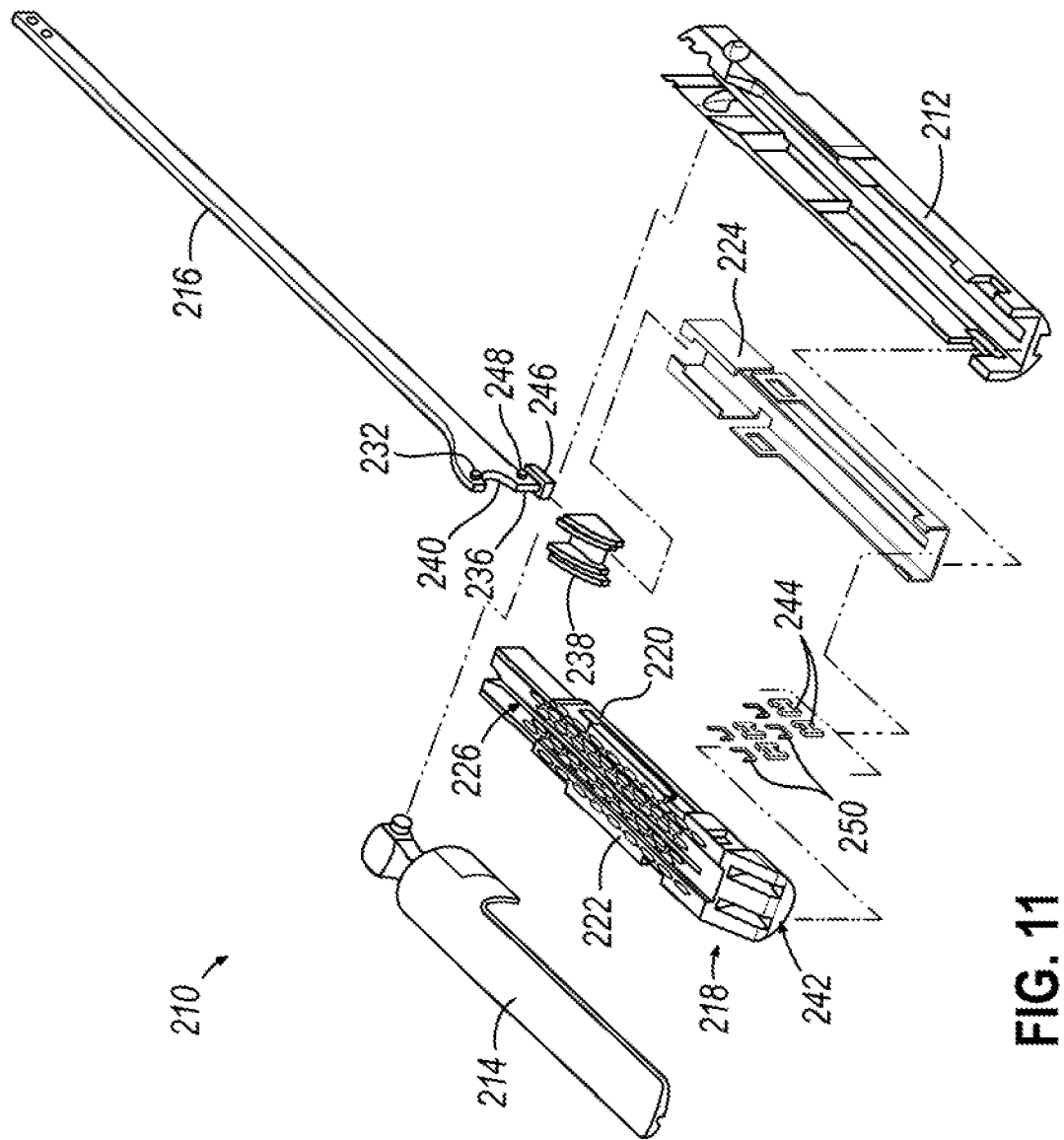
FIG. 11 depicts an exploded view of the end effector of FIG. 10.

FIGS. 10-11 show a second exemplary end effector (210), in an open position, that is configured to compress, cut, and staple tissue. End effector (210) may be configured for use with surgical instrument (110) of FIG. 4, or with surgical instruments of alternative constructions. End effector (210) may be constructed and operable in accordance with at least some of the teachings of U.S. patent application Ser. No. 16/916,295, entitled "Surgical Stapler Cartridge Retainer with Ejector Feature," filed Aug. 3, 2020, issued as U.S. Pat. No. 11,497,494 on Nov. 15, 2022, the disclosure of which is incorporated by reference herein in its entirety. End effector (210) of the present example includes a lower jaw (212) and an upper jaw in the form of a pivotable anvil (214). Lower jaw (212) may be constructed and operable in accordance with at least some of the teachings of U.S. Pat. No. 9,808,248, entitled "Installation Features for Surgical Instrument End Effector Cartridge," issued Nov. 7, 2017, the disclosure of which is incorporated by reference herein in its entirety. Anvil (214) may be constructed and operable in accordance with at least some of the teachings of U.S. Pat. No. 10,092,292, entitled "Staple Forming Features for Surgical Stapling Instrument," issued Oct. 9, 2018, the disclosure of which is incorporated by reference herein in its entirety.

FIG. 10 shows end effector (210), where anvil (214) is pivoted to an open position and a firing beam (216) is proximally positioned, allowing an unspent staple cartridge (218) to be removably installed into a channel of lower jaw (212). Staple cartridge (218) includes a cartridge body (220), which presents an upper deck (222) and is coupled with a lower cartridge tray (224). A vertical slot (226) is formed through part of staple cartridge (218) and opens upwardly through upper deck (222). One or more rows of staple apertures (228) are formed through upper deck (222) on one side of vertical slot (226), with one or more rows of staple apertures (228) being formed through upper deck (222) on the other side of vertical slot (226). End effector (210) is closed by distally advancing a closure tube (not shown) and a closure ring (230). Firing beam (216) is then advanced distally so that an upper pin of firing beam (216) enters longitudinal anvil slot (234). Simultaneously, a pusher block (236) located at the distal end of firing beam (216) engages a wedge sled (238) housed within cartridge body (220), such that wedge sled (238) is pushed distally by pusher block (236) as firing beam (216) is advanced distally through staple cartridge (218) and anvil (214).

During firing, cutting edge (240) of firing beam (216) enters vertical slot (226) toward distal end (242) of staple cartridge (218), severing tissue clamped between staple cartridge (218) and anvil (214). As best seen in FIG. 11, wedge sled (238) presents inclined cam surfaces that urge staple drivers (244) upwardly as wedge sled (238) is driven distally through staple cartridge (218). A firing beam cap (246) slidably engages a lower surface of lower jaw (212). Wedge sled (238) is movable longitudinally within staple cartridge (218), while staple drivers (244) are movable vertically within staple cartridge (218). A middle pin (248) and pusher block (236) of firing beam (216) together actuate staple cartridge (218) by entering into vertical slot (226) within staple cartridge (218), driving wedge sled (238) distally into upward camming contact with staple drivers (244) that in turn drive staples (250) out through staple apertures (228) and into forming contact with staple forming pockets (252) on the inner surface of anvil (214). Additional examples of alternative surgical instruments and/or associated features are described in U.S. patent application Ser. No. 16/946,363, entitled "Articulation Mechanisms for Robotic Surgical Tools," filed on Jun. 18, 2020, issued as U.S. Pat. No. 11,896,202 on Feb. 13, 2024, the disclosure of which is hereby incorporated by reference herein in its entirety.

It will be appreciated that any one or more of the teachings described below may be combined with any one or more of the teachings described above in connection with FIGS. 1-11.

II. Exemplary Firing Lockout Features for Surgical Staplers

In some instances, it may be desirable to provide one or more components of the firing system of an end effector (116, 210), such as one or more of lower jaw (152), staple cartridge (154, 218), wedge sled (170, 238), and/or staple drivers (160, 244), with multiple features to separately and independently monitor a status of the staple cartridge (154, 218). The separate status signals from the independent monitoring features may therefore be corroborated before a firing is initiated.

Some systems may utilize spring biased or positioned biased mechanical lockouts as a positive means to ensure that a spent staple cartridge without staples, or a staple cartridge that is incompatible with the end effector, to inhibit firing (which would result in cut tissue without proper sealing of the tissue). For systems using a single-point-of-failure electronic lockout, the safety system may tend to erroneously disable the safety system. If a single safety monitor sensor is utilized, an incorrect signal from the sensor or a failure of the sensing electronics could result in the lack of signal or wrong signal that might still enable a staple firing under unsafe conditions. Likewise, an overly sensitive monitoring system that errs by initiating safety lockouts of unspent compatible staple cartridges may also provide operational concerns.

Accordingly, as described herein, multiple monitoring features may be configured to assist in minimizing unsatisfactory performance of staple cartridge (154, 218), such as by monitoring for any one or more of: errors in staple cartridge (154, 218) positioning; whether staple cartridge (154, 218) has been fired previously such that staple cartridge (154, 218) is "spent" (i.e., staples (162, 250) have already been deployed from staple cartridge (154, 218)); the compatibility of staple cartridge (154, 218) with instrument (26, 110) or end effector (116, 210); or other details of staple cartridge (154, 218). To that end, various features are described below for providing one or more of these functionalities.

It will be appreciated that in some versions, a first monitoring feature may be provided to detect a first condition of staple cartridge (154, 218) and/or lower jaw (152) that warrants a firing lockout state, and a second monitoring feature may be provided to independently detect a second condition of staple cartridge (154, 218) and/or lower jaw (152) that likewise warrants a firing lockout state. In other versions, a first monitoring feature may be provided to detect a condition of staple cartridge (154, 218) and/or lower jaw (152) that warrants a firing lockout state, and a second monitoring feature may be operatively coupled with and configured to detect whether the first monitoring feature is operating correctly.

A. Exemplary Lower Jaw Monitoring Features Using RFID

Lower cartridge tray (177, 224) can include various lower jaw (152) monitoring features adapted to monitor one or more conditions of the lower jaw (152) such, for example, the existence of staple cartridge (154, 218), the status of the staple cartridge (154, 218) (i.e., whether it has been spent), proper placement of the staple cartridge (154, 218) (i.e., ensuring the staple cartridge is properly seated within the channel), and/or the positioning of the wedge sled (170, 238) within the lower jaw (152).

Figure 12:
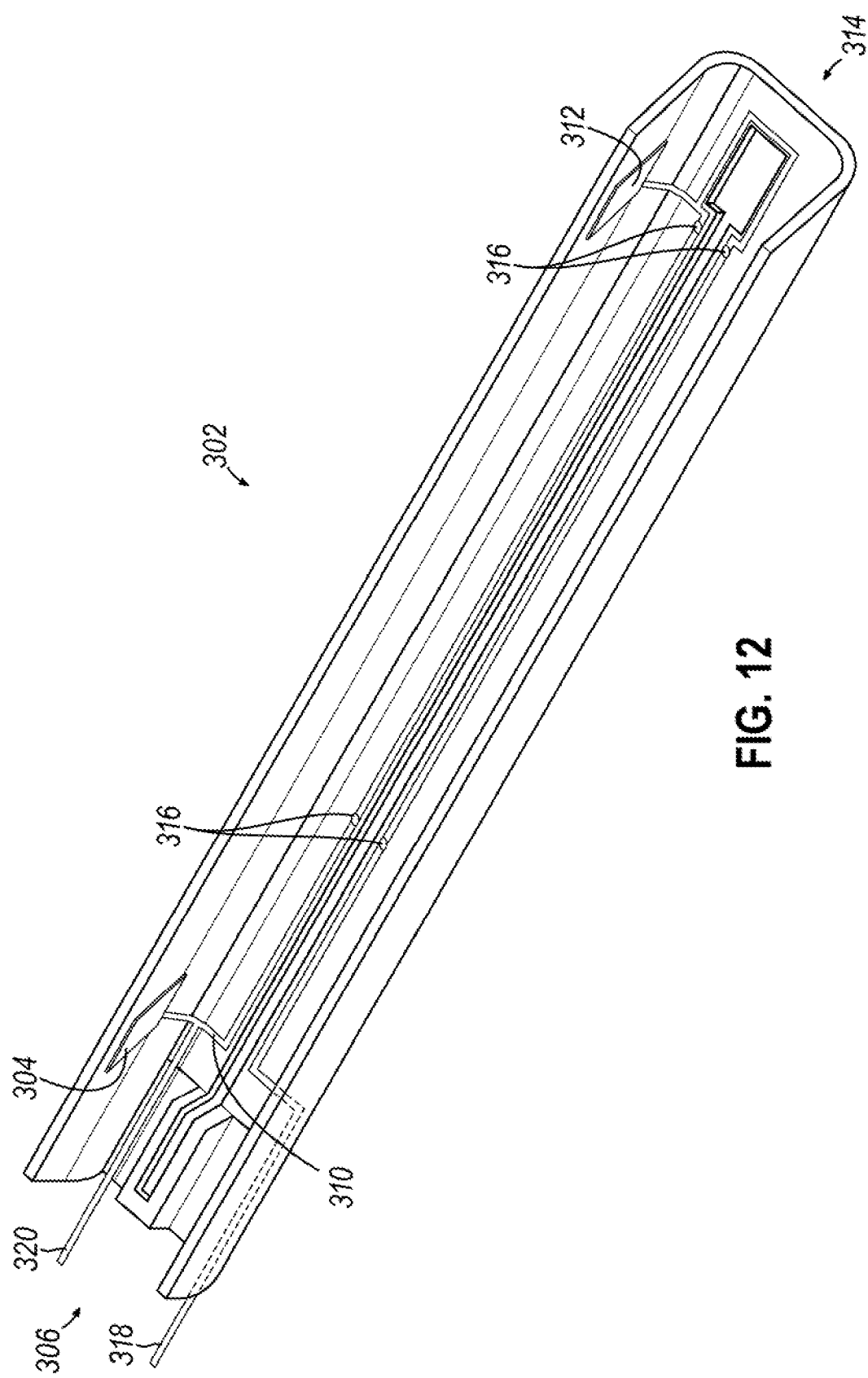
FIG. 12 depicts a perspective view of a first exemplary alternative lower cartridge tray shown removed from a surgical instrument end effector.

FIG. 12 shows an exemplary lower cartridge tray (302) which forms a part of an end effector (360) (see FIG. 13), end effector (360) and lower cartridge tray (302) each being configured to provide similar functions as end effectors (116, 210) and lower cartridge trays (177, 224) except as described below. Particularly, lower cartridge tray (302) can include an RFID power coil (304) at the proximal end (306) of the lower cartridge tray (302) that is configured to communicate with an RFID tag (308) that is positioned on the wedge sled (350) (see FIG. 14). Wedge sled (350) of staple cartridge (154, 218) is configured to operate similar to wedge sleds (170, 238) described above. RFID power coil (304) may be powered by a flex circuit, such as flex circuit (310), by wiring, or by any other known methods of powering and RFID system. In some versions, lower cartridge tray (302) can include a second RFID power coil (312) at the distal end (314) of lower cartridge tray (302) that is also configured to communicate with the RFID tag (308) on wedge sled (350). To power RFID power coils (304, 312), flex circuit (310) is electrically coupled with and driven by a portion of robotic surgical system (10), such as electronics cart (24) or processor (38).

In some versions, lower cartridge tray (302) can include one or more electrical contacts (316) arranged along the length of lower cartridge tray (302) that are configured to monitor proper placement of staple cartridge (352) (see FIG. 13) within lower cartridge tray (302). For example, as staple cartridge (352) is positioned into lower cartridge tray (302), the one or more electrical contacts (316) are configured to interact with portions (354) of the staple cartridge (352) disposed on the lower surface (356) of staple cartridge (352) to indicate to robotic surgical system (10) or surgical instrument (26, 110) that staple cartridge (352) is seated properly. In one version, the one or more electrical contacts (316) are formed as non-conductive gaps in the electrical path provided by flex circuit (310) which are conductively bridged by corresponding portions (354) of staple cartridge (352), such a protrusions, as staple cartridge (352) is seated into lower cartridge tray (302). Accordingly, corresponding portions (354) of staple cartridge (352) may be formed with conductive traces for bridging the non-conductive gaps of electrical contacts (316). Therefore, as staple cartridge (352) is seated into lower cartridge tray (302), an electrical path is completed by flex circuit (310) and electrical contacts (316) thereby allowing current flow between electrical leads (318, 320). As seen by robotic surgical system (10) or surgical instrument (26, 110), electrical current flow through flex circuit (310) is indicative of the presence of staple cartridge (352) and also proper seating of staple cartridge (352).

Figure 13:
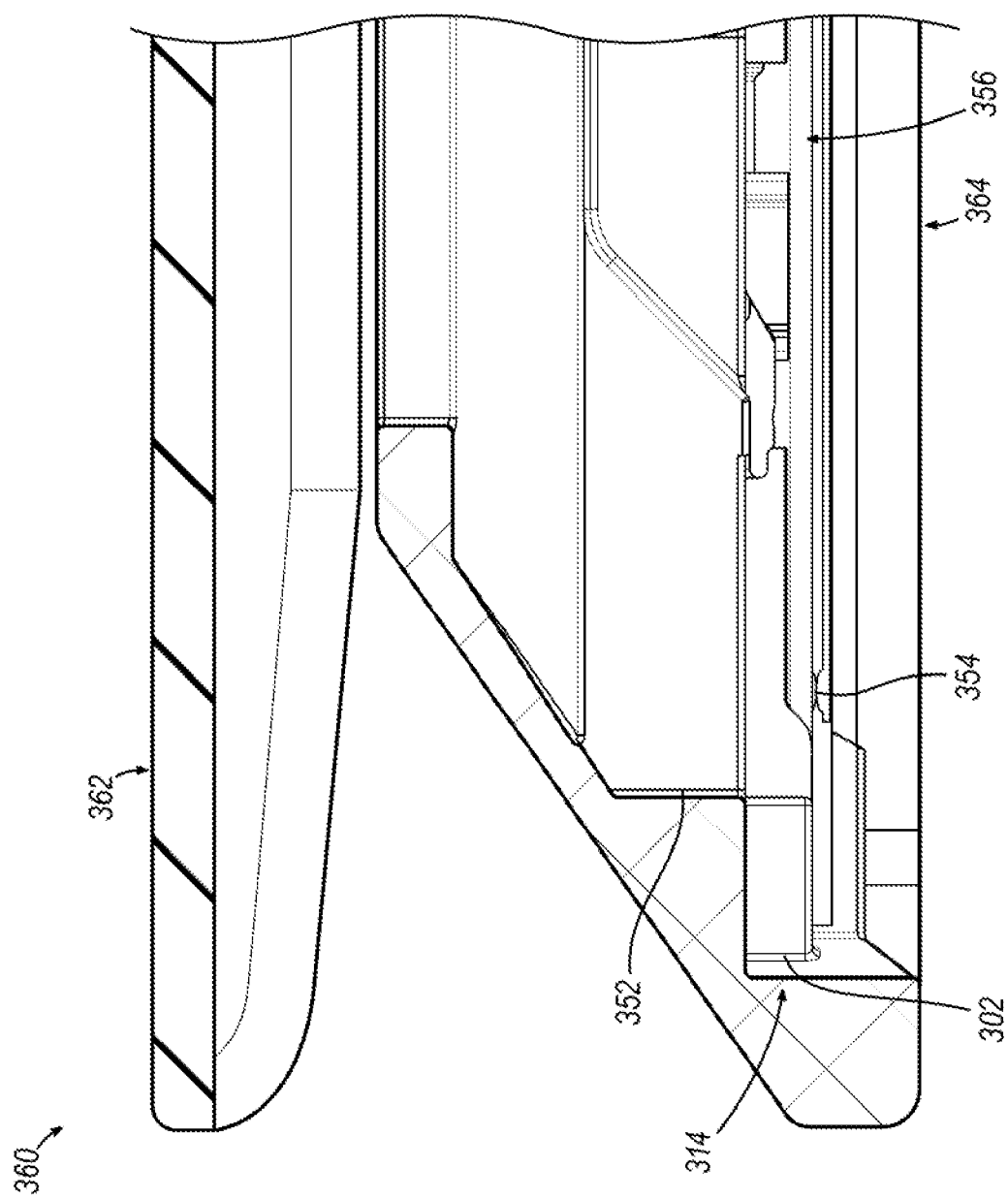
FIG. 13 depicts a cross-sectional view of a distal portion of an exemplary end effector having the lower cartridge tray of FIG. 12 disposed therein, the lower cartridge tray further having a staple cartridge installed therein.

An alternative example is depicted in FIG. 13. As shown in FIG. 13, staple cartridge (352) is installed on an end effector (360) having an upper jaw (362) and a lower jaw (364), the staple cartridge (352) installed on the lower jaw (364). In this version, the one or more electrical contacts (316) arranged along the length of staple cartridge (352) are configured with electrical switches operable as push buttons. Optionally, lower surface (356) of staple cartridge (352) can include corresponding portions (354) shaped as protrusions for pressing the push-button electrical contacts (316) as staple cartridge (352) is aligned and properly seated on lower cartridge tray (302). Alternatively, lower surface (356) of staple cartridge (352) may be shaped to press contacts as it seats into lower cartridge tray (302) without the need for any protrusions.

Figure 15A:
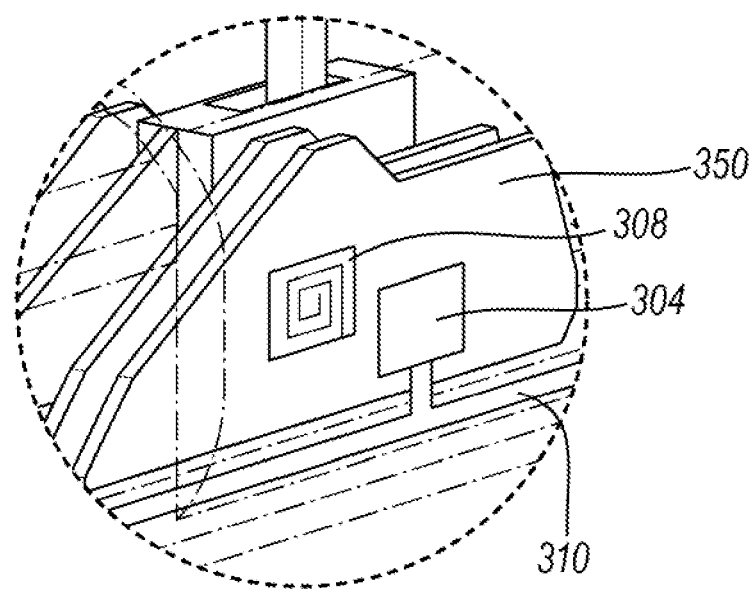
FIG. 15A depicts an enlarged perspective view of a portion of the end effector of FIG. 13 with portions thereof shown in broken lines to reveal internal features, showing the wedge sled in a proximal, un-fired position.
Figure 15B:
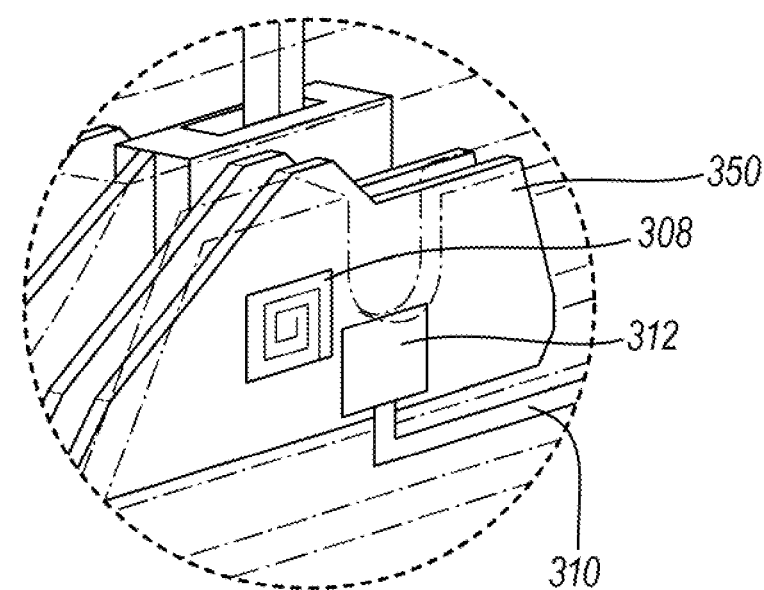
FIG. 15B depicts an enlarged perspective view of the end effector of FIG. 13 with portions thereof shown in broken lines to reveal internal features, showing the wedge sled in a distal, fired position.

Depicted in FIG. 14 is lower cartridge tray (302) and staple cartridge (352) showing portions of staple cartridge (352) removed for clarity. Particularly, as described with reference to FIG. 12, lower cartridge tray (302) includes a first RFID power coil (304) and a second RFID power coil (312) each configured to interact with RFID tag (308) of staple cartridge (352). RFID tag (308) is placed, for example, on wedge sled (350) of staple cartridge (352), and specifically on an outer-facing surface (358) of wedge sled (350) to thereby align with and communicate with RFID power coils (304, 312) depending on the longitudinal positioning of wedge sled (350) within staple cartridge (352). In operation, as depicted in FIG. 15A, staple cartridge (352) is first placed into lower cartridge tray (302). In accordance with the description above, flex circuit (310) may be included with one or more electrical contacts (316) (see FIG. 12) to ensure proper placement and alignment of staple cartridge (352). In some versions, the completed electrical circuit of the flex circuit (310) may operate to provide power to each RFID power coil (304, 312), while in alternative versions the RFID power coils (304, 312) may be independently powered. Once surgical instrument (26, 110) has determined that staple cartridge (352) is properly seated, proximal RFID power coil (304) is powered on and configured to read RFID tag (308) on wedge sled (350). RFID tag (308) on wedge sled (350) may provide various staple cartridge (352) information including, but not limited to, the color, size, serial number, and/or firing status. Firing status may be indicated by RFID tag (308) having a memory storing a digital count value. For example, the initial default count value provided to RFID tag (308) at the time of manufacturing may be 1. After firing and expending the staple cartridge (352), as will be described below, distal RFID power coil (312) is configured to write to RFID tag (308) to incrementally increase the count value by 1 to become 2. Thereafter, if staple cartridge (352) is inserted into lower jaw (364) of end effector (360) after having been spent and storing a count value of 2, proximal RFID power coil (304) will recognize the count value being greater than 1 and initiate a lockout of surgical instrument (26, 110) to prevent an errant firing of the spent staple cartridge (352). Depicted in FIG. 15B is wedge sled (350) positioned at distal end (314) of staple cartridge (352) as result of a firing stroke to apply staples. Once distal RFID power coil (312) detects RFID tag (308) in proximity and provides initiation power to RFID tag (308), distal RFID power coil (312) writes to RFID tag (308) to increase the count value as described above.

B. Exemplary Lower Jaw Monitoring Features Using Electrical Continuity

Figure 16:
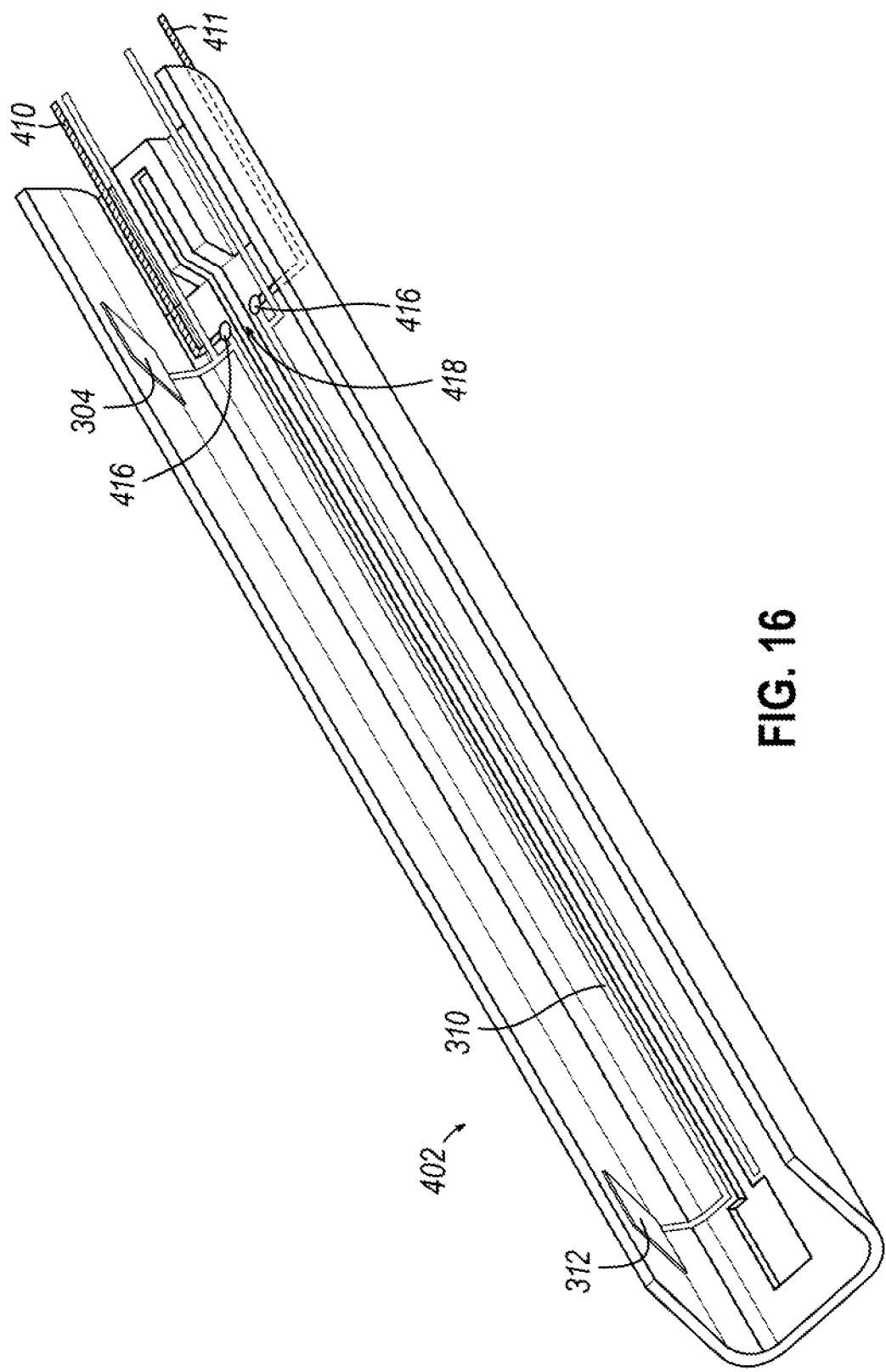
FIG. 16 depicts a perspective view of a second exemplary alternative lower cartridge tray shown removed from a surgical instrument end effector.
Figure 17:
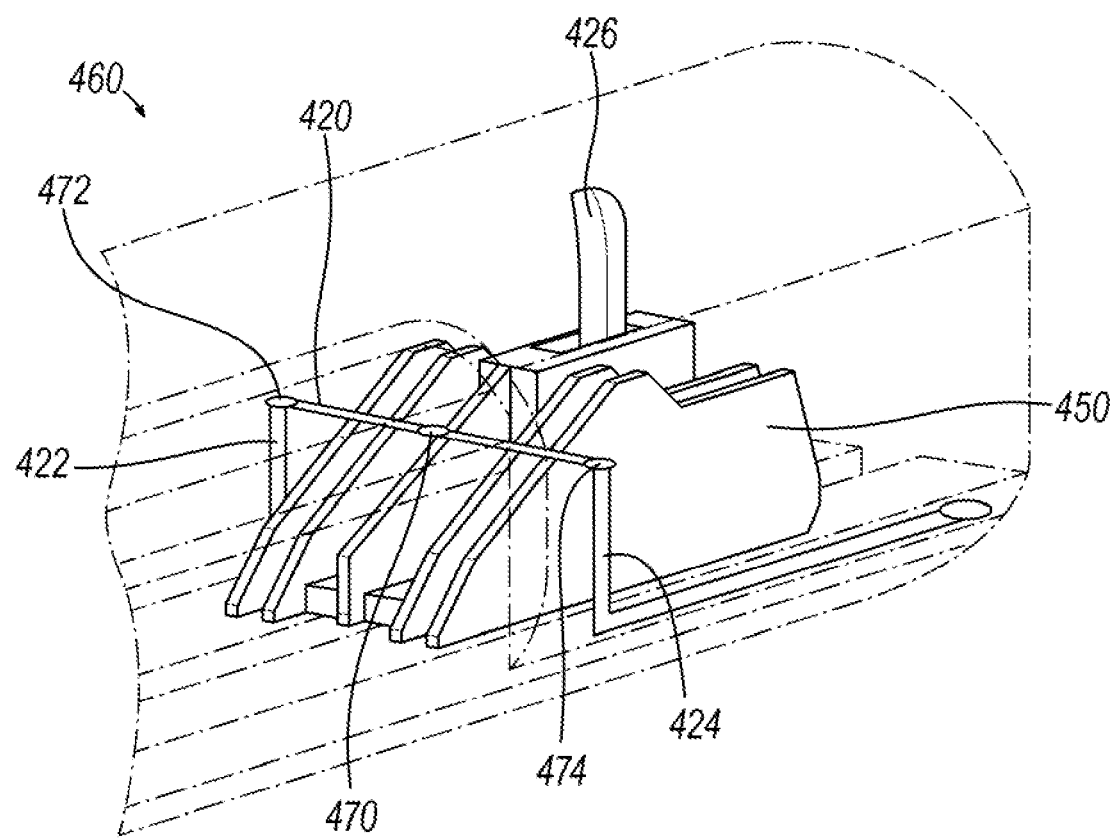
FIG. 17 depicts an enlarged perspective view of a portion of an end effector having the lower cartridge tray of FIG. 17 disposed therein, with portions of the end effector shown in broken lines to reveal internal features, showing a wedge sled in a proximal, un-fired position.

FIGS. 16-17 show another exemplary lower cartridge tray (402) which forms a part of an end effector (460) (see FIG. 17), end effector (460) and lower cartridge tray (402) each being configured to provide similar functions as end effectors (116, 210, 360) lower cartridge trays (177, 224, 302) except as described below. Particularly, in addition or alternative to RFID power coils (304, 312), RFID tag (308), and flex circuit (310), lower cartridge tray (402) may include additional monitoring features for detecting the presence or status of a staple cartridge (452) (see FIGS. 18A-18B) positioned therein. For example, as will be described in greater detail below, lower cartridge tray (402) and staple cartridge (452) may cooperate to form an electrical continuity fuse feature (420) configured to indicate the spent or unspent status of staple cartridge (452). Further, similar to staple cartridge (352) described above, staple cartridge (452) can include a flex circuit (410, 411) with one or more electrical contacts (416) to ensure proper seating of staple cartridge (452) within lower cartridge tray (402).

More particularly, as shown in FIG. 16, lower cartridge tray (402) may include an additional flex circuit (410, 411) having paths for coupling with a power source (not shown), such as electronics cart (24) or processor (38), and electrical contacts (416) separated by a gap (418) or alternatively by non-conductive material. As such, prior to seating staple cartridge (452), electrical current is unable to flow from flex circuit (410) to flex circuit (411) across gap (418).

As depicted in FIG. 17, wedge sled (450) of staple cartridge (452) includes a continuity fuse feature (420) for detecting whether staple cartridge (452) has been previously spent. Continuity fuse feature (420) may be formed of any conductive material. Optionally, continuity fuse feature (420) may include a protective, non-conductive coating (not shown) over the conductive material to prevent electrical current from making contact with other portions of staple cartridge (452) or lower cartridge tray (402). Continuity fuse feature (420) includes electrical paths of flex circuits (422, 424) configured to contact and electrically couple each electrical contact (416), thereby completing an electrical circuit between paths of flex circuits (410, 411) while in the un-fired position. Particularly, as described above, wedge sled (450) advances distally during firing. Accordingly, continuity fuse feature (420) may be disposed across an upper portion of wedge sled (450) while wedge sled (450) is posited in the proximal, un-fired position such that knife (426) breaks continuity fuse feature (420) during a firing stroke. Thereafter, electrical current is unable to flow through the electrical path formed by flex circuit (410, 411), electrical contacts (416), and continuity fuse feature (420), indicate to robotic surgical system (10) or surgical instrument (26, 110) that staple cartridge (452) has been spent. Upon robotic surgical system or surgical instrument (26, 110) determining staple cartridge has been spent, robotic surgical system or surgical instrument (26, 110) may initiate a lockout procedure to prevent additional firings.

Figure 18A:
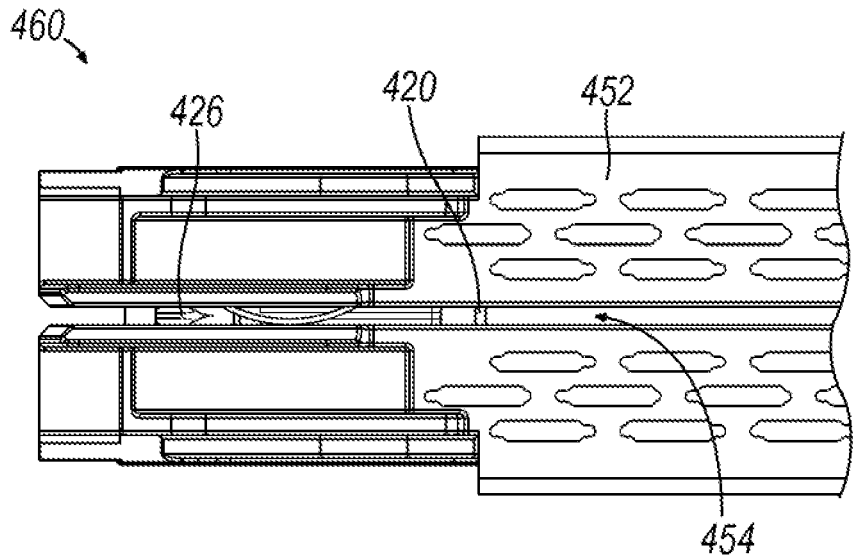
FIG. 18A depicts a top plan view of a proximal portion of a staple cartridge of the end effector of FIG. 17, showing the wedge sled in a proximal, un-fired position.
Figure 18B:
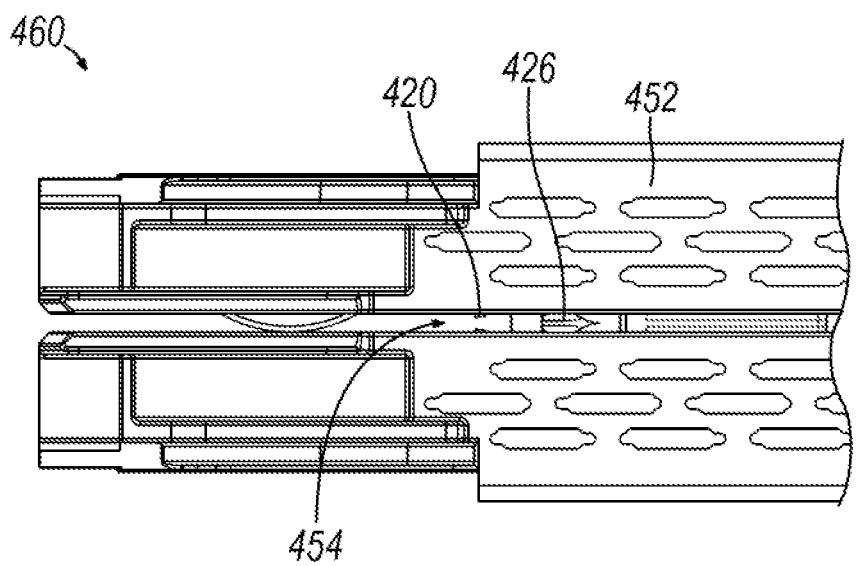
FIG. 18B depicts a top plan view of the proximal portion of the staple cartridge of FIG. 18A, showing the wedge sled in a mid-firing position.

FIG. 18A depicts an overview of staple cartridge (452) in an unfired position whereby continuity fuse feature (420) is bridged across knife slot (454). During a staple firing, as depicted in FIG. 18B, knife (426) advances distally and breaks through continuity fuse feature (420). Once continuity fuse feature (420) has been broken, electrical connectivity between paths of flex circuits (410, 411) has been broken thereby indicating to robotic surgical system (10) or surgical instrument (26, 110) that staple cartridge (452) has been spent. In some versions, continuity fuse feature (420) may be one-time use, while in other versions, continuity fuse feature (420) may include a latch (470) and hinge features (472, 474)) (see FIG. 17) that cooperatively allow continuity fuse feature (420) to be reset. For instance, continuity fuse feature (420) may be reset if staple cartridge (452) is recycled and reloaded with staples for future use.

C. Exemplary Lower Jaw Monitoring Features Using Wedge Sled Sensors

Figure 19:
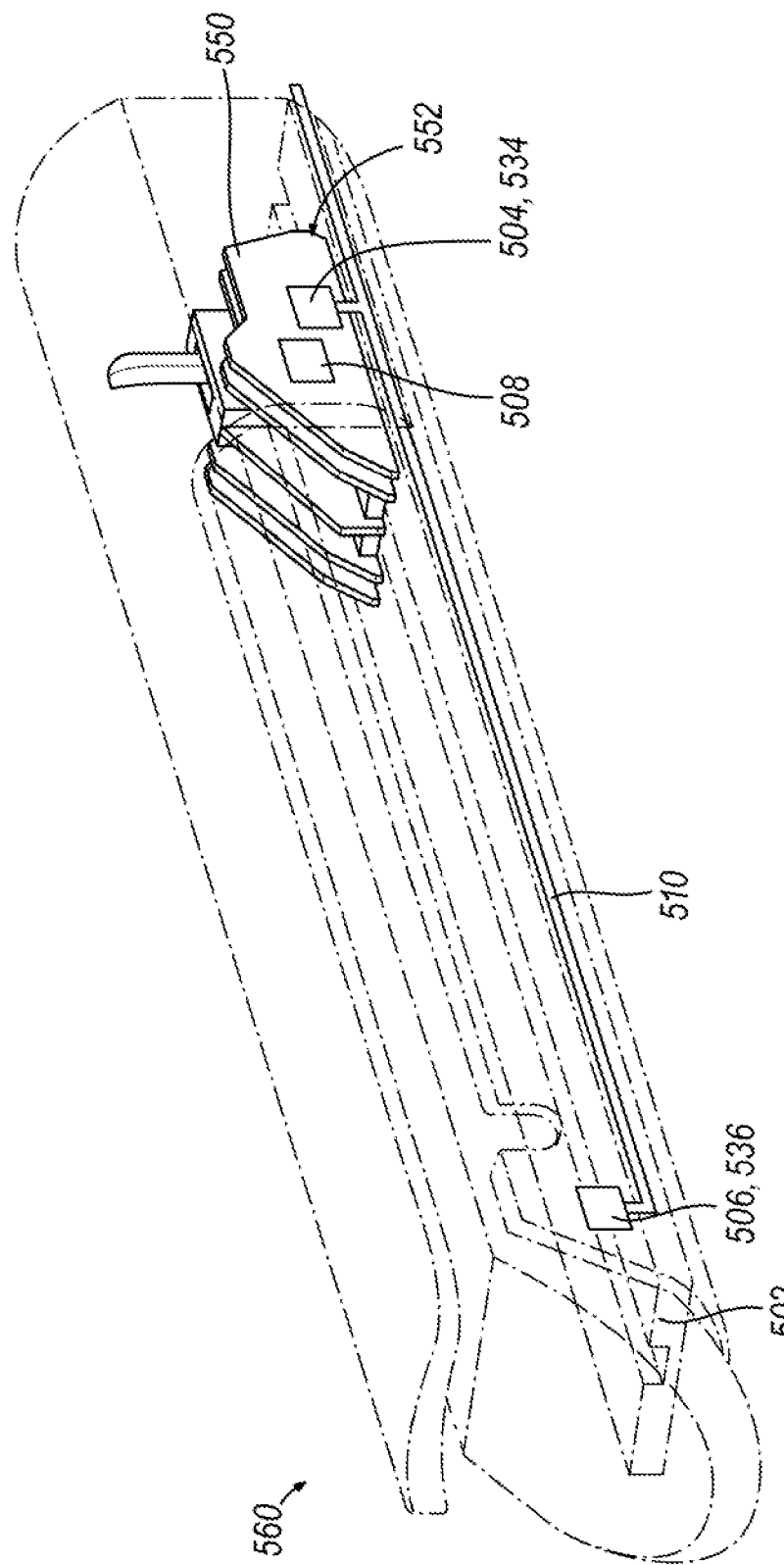
FIG. 19 depicts a perspective view of another exemplary end effector with portions thereof shown in broken lines to reveal internal features, showing a third exemplary alternative lower cartridge tray installed therein.

FIG. 19 shows another exemplary end effector (560) having a lower cartridge tray (502) configured to provide similar functions as end effectors (116, 210, 360, 460) and lower cartridge trays (177, 224, 302, 402) except as described below. Particularly, in addition or alternative to RFID power coils (304, 312), RFID tag (308), flex circuits (310, 410, 411), land continuity fuse feature (420), lower cartridge tray (502) may include additional monitoring features for detecting the presence or status of a staple cartridge.

In the exemplary version shown, lower cartridge tray (502) includes a flex circuit (510) disposed along the length of lower cartridge tray (502) for coupling one or more hall effect sensors to robotic surgical system (10), such as electronics cart (24) or processor (38). Hall effect sensors (504, 506) are configured to detect the presence of a magnet (508) disposed in close proximity and transmit a signal back to robotic surgical system (10) via flex circuit (510) indicating the presence of magnet (508) adjacent one of the hall effect sensors (504, 506). To that end, magnet (508) may be positioned on wedge sled (550), such as on an outer-facing surface (552) of wedge sled (550) adjacent hall effect sensors (504, 506), such that wedge sled (550) translates magnet (508) from a proximal first position adjacent proximal hall effect sensor (504) prior to a firing stroke to a distal second position adjacent distal hall effect sensor (506) after a firing stroke. By determining wedge sled (550) is positioned adjacent proximal hall effect sensor (504), robotic surgical system (10) may determine the staple cartridge containing wedge sled (550) is in an unfired state. By determining wedge sled (550) is positioned adjacent distal hall effect sensor (506), robotic surgical system (10) may determine the staple cartridge containing wedge sled (550) is in a fired state and may initiate a firing lockout. In an alternative version, magnet (508) is integrated inside wedge sled (550).

In another version, referencing FIG. 19, lower cartridge tray (502) may include flex circuit (510) disposed along the length of lower cartridge tray (502) for coupling one or more inductive sensors (534, 536) to robotic surgical system (10), such as electronics cart (24) or processor (38). Inductive sensors (534, 536) are configured to detect the presence of metal, such as a metal wedge sled (550) or metal staples within staple cartridge disposed in close proximity to inductive sensors (534, 536) and transmit a signal back to robotic surgical system (10) indicating the presence of the metal adjacent one of inductive sensors (534, 536). Wedge sled (550) translates from a first position adjacent proximal inductive sensor (534) prior to a firing stroke to a second position adjacent distal inductive sensor (536) after a firing stroke. By determining wedge sled (550) is positioned adjacent proximal inductive sensor (534), robotic surgical system (10) may determine staple cartridge containing wedge sled (550) is in an unfired state. By determining wedge sled (550) is positioned adjacent distal inductive sensor (536), robotic surgical system (10) may determine staple cartridge containing wedge sled (550) is in a fired state and initiate a firing lockout. In some versions, wedge sled (550) is formed of a definitive metal have a unique inductive signature. Inductive sensors (534, 536) in this version are used to verify staple cartridge has a full staple load.

III. Exemplary Firing Circuits for Surgical Staplers

While various alternative lockout monitoring features have been described above, it should be understood that two or more unique lockout monitoring features may be utilized concurrently and monitored independently. By monitoring two or more sensor features independently and corroborating the sensed status indicators as described above, additional care may be taken to ensure errors are avoided during a surgical procedure.

Figure 20:
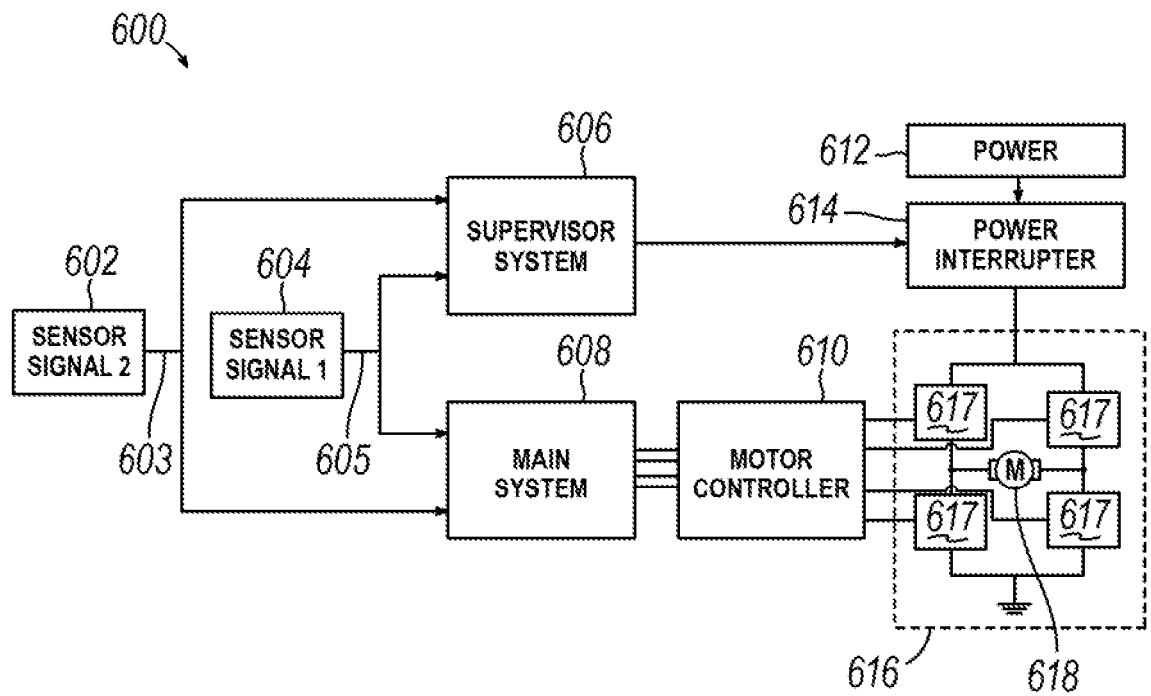
FIG. 20 depicts a schematic view of a first exemplary firing circuit adapted for receiving signals from a plurality of lockout monitoring features and selectively powering an end effector.

To that end, depicted in FIG. 20 is an exemplary staple firing circuit (600). As described above, multiple lockout monitoring sensors (602, 604) may be included in an end effector, such as end effector (116), and particularly incorporated within the lower jaw (152) thereof, to separately and independently monitor the status of a staple cartridge (154) and provide two or more output signals (603, 605) indicative of such so they may be corroborated prior to firing. First lockout monitoring output signal (603) and second lockout monitoring output signal (605) are each split between a main processor (608) and a supervising processor (606). Main processor (608) is configured to drive motor controller (610), which is configured to drive a motor firing circuit (616) coupling a power source (612) to motor (618). Motor firing circuit (616) may include, for example, various electrical components (617) such as transistors for selectively connecting and disconnecting motor (618) to power source (612) at the direction of motor controller (610). Main processor (608) is configured to receive first lockout monitoring output signal (603) and second lockout monitoring signal (605) and determine whether each signal (603, 605) indicates the end effector, particularly the staple cartridge installed within the end effector, is prepared for operation. If the signals (603, 605) do not indicate the end effector is prepared for operation, main processor (608) controls motor controller (610) to initiate a lockout condition on motor firing circuit (616) to prevent a staple firing operation.

Supervising processor (606) is configured to receive first lockout monitoring output signal (603) and second lockout monitoring signal (605) and redundantly determine whether each signal (603, 605) indicates the end effector, particularly the staple cartridge installed within the end effector, is prepared for operation. If the signals (603, 605) do not indicate the end effector is prepared for operation, supervising processor (606) operates a power interrupter to disconnect power source (612) from motor firing circuit (616). Accordingly, circuit (600) is configured to receive redundant safety condition signals from multiple independent lockout monitoring features prior to permitting a staple firing operation. If either safety condition signal indicates an unsafe condition, circuit (600) is configured to initiate a motor firing lockout.

Figure 21:
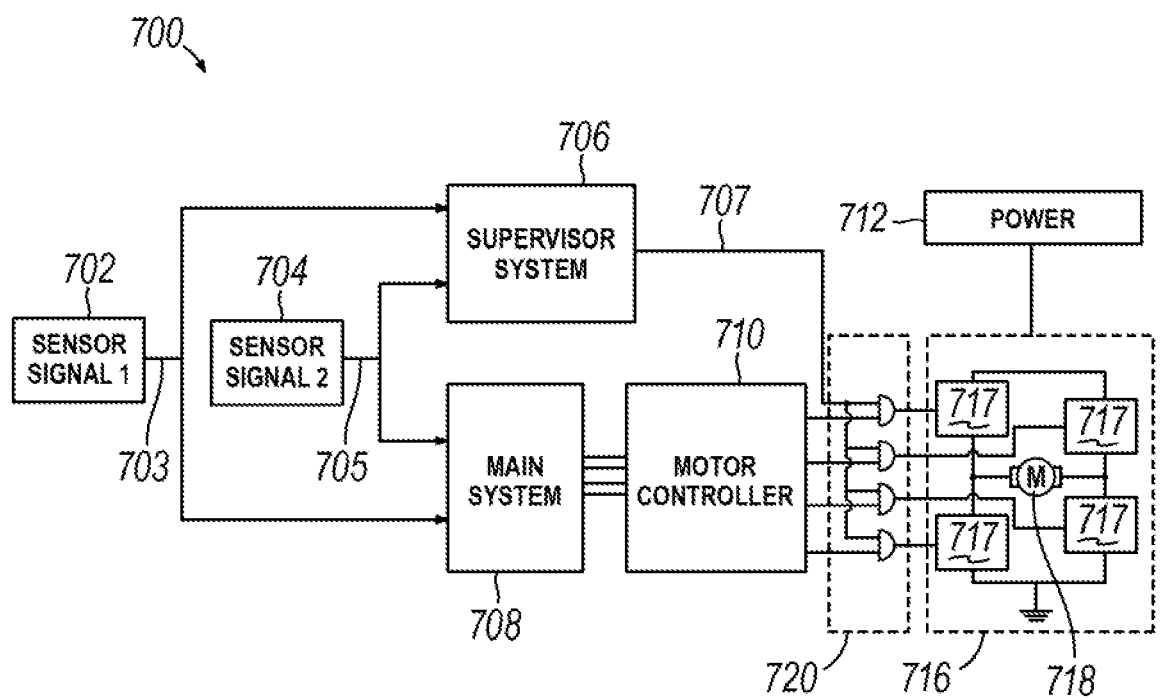
FIG. 21 depicts a schematic view of a second exemplary firing circuit adapted for receiving signals from a plurality of lockout monitoring features and selectively powering an end effector.

Depicted in FIG. 21 is an exemplary alternative staple firing circuit (700). As described above, redundant lockout monitoring features may be included in the end effector, such as end effector (116), and particularly incorporated within the lower jaw (152), to monitor the status of a staple cartridge (154) and provide two or more output signals (703, 705) indicative of such. First lockout monitoring output signal (703) and second lockout monitoring output signal (705) are each split between a main processor (708) and a supervising processor (706). Main processor (708) is configured to drive motor controller (710), which is configured to drive a motor firing circuit (716) via digital logic gates (720) coupling a power source (712) to motor (718). Motor firing circuit (716) may include, for example, various electrical components (717) such as transistors for selectively connecting and disconnecting motor (718) to power source (712) at the direction of motor controller (710). Main processor (708) is configured to receive first lockout monitoring output signal (703) and second lockout monitoring signal (705) and determine whether each signal (703, 705) indicates the end effector, particularly staple cartridge installed within the end effector, is prepared for operation. If the signals (703, 705) do not indicate the end effector is prepared for operation, main processor (708) controls motor controller (710) to initiate a lockout condition on motor firing circuit (716) to prevent a staple firing operation.

Supervising processor (706) is configured to receive first lockout monitoring output signal (703) and second lockout monitoring signal (705) and redundantly determine whether each signal (703, 705) indicates the end effector, particularly staple cartridge installed within the end effector, is prepared for operation. If the signals (703, 705) do not indicate the end effector is prepared for operation, supervising processor (706) outputs a signal (707) to digital logic gates (720) sufficient to initiate a lockout condition on motor firing circuit (716) to prevent a staple firing operation. Accordingly, circuit (700) is configured to receive redundant signals from multiple independent lockout monitoring features prior to permitting a staple firing operation. If either safety condition signal indicates an unsafe condition, circuit (700) is configured to initiate a motor firing lockout.

It will be further appreciated that any of the exemplary features described above in connection with FIGS. 12-21 may be employed to ensure compatibility of a particular staple cartridge (154) with a given end effector (116) before a firing stroke is performed. For instance, end effector (116) may include a detection feature, which may employ RFID technology for example, configured to detect a type of staple cartridge (154) loaded into lower jaw (152) and compare the detected type to one or more predetermined types acceptable for use with end effector (116). If the detected type is not among the predetermined acceptable types, the surgical instrument and/or robotic surgical system (10) may determine that the staple cartridge (154) is incompatible for use with end effector (116) and subsequently engage a firing lockout mechanism to inhibit firing of end effector (116) on tissue with the incompatible staple cartridge (154). In this manner, robotic surgical system (10) may ensure that a surgical stapling procedure performed with end effector (116) is performed accurately without comprising the resulting arrays of staples formed into the patient tissue.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical stapling instrument, comprising: (a) a shaft assembly extending along a longitudinal axis to a distal end; (b) an end effector at the distal end of the shaft assembly, wherein the end effector includes: (i) a first jaw having an anvil, and (ii) a second jaw, wherein the first and second jaws are operable to clamp tissue therebetween; (c) a cartridge insertable into the second jaw of the end effector, wherein the cartridge includes: (i) a plurality of staples, (ii) a movable member translatable distally through the cartridge during a firing stroke of the end effector to discharge the plurality of staples into the tissue, (iii) a first sensor assembly configured to monitor a first condition of the cartridge when the cartridge is inserted into the second jaw of the end effector, and (iv) a second sensor assembly configured to monitor a second condition of the cartridge when the cartridge is inserted into the second jaw of the end effector; and (d) a first processor coupled with the first sensor assembly and the second sensor assembly, wherein the first processor is configured to receive a first signal from the first sensor assembly indicative of the first condition of the cartridge and a second signal from the second sensor assembly indicative of the second condition of the cartridge, wherein the first processor is configured to selectively permit or restrict the firing stroke based upon the first signal and the second signal.

Example 2

The surgical stapling instrument of Example 2, wherein the processor is configured to monitor the first signal and the second signal independently, wherein the processor is configured to restrict the firing stroke based upon either the first signal or the second signal indicating a negative condition of the cartridge.

Example 3

The surgical stapling instrument of Example 2, wherein the negative condition of the cartridge includes at least one of a first negative condition, a second negative condition, or a third negative condition, wherein the first negative condition is indicative of the cartridge being improperly inserted into the second jaw of the end effector, wherein the second negative condition is indicative of the cartridge being spent, wherein the third negative condition is indicative of the cartridge being incompatible with the end effector.

Example 4

The surgical stapling instrument of any of the preceding Examples, wherein the first condition of the cartridge and the second condition of the cartridge are the same.

Example 5

The surgical stapling instrument of any of the preceding Examples, wherein the first condition of the cartridge and the second condition of the cartridge are different.

Example 6

The surgical stapling instrument of any of the preceding Examples, further comprising a second processor coupled with the first sensor assembly and the second sensor assembly, wherein the second processor is configured to receive the first signal from the first sensor assembly indicative of the first condition of the cartridge and the second signal from the second sensor assembly indicative of the second condition of the cartridge, wherein the second processor is configured to selectively permit or restrict the firing stroke based upon the first signal and the second signal.

Example 7

The surgical stapling instrument of any of the preceding Examples, wherein one of the first sensor assembly or the second sensor assembly includes a first RFID power coil and an RFID tag, wherein the first RFID power coil is disposed on the second jaw of the end effector and the RFID tag is disposed on the movable member, wherein the first RFID power coil is operable to read a set of cartridge information from the RFID tag.

Example 8

The surgical stapling instrument of any of Example 7, wherein the one of the first sensor assembly or the second sensor assembly includes a second RFID power coil, wherein the first RFID power coil is disposed at a proximal position of the second jaw, wherein the second RFID power coil is disposed at a distal position of the second jaw.

Example 9

The surgical stapling instrument of Example 8, wherein the second RFID power coil is operable to write to the RFID tag, wherein upon the completion of the firing stroke the second RFID power coil is configured to write to the RFID tag.

Example 10

The surgical stapling instrument of any of the preceding Examples, wherein one of the first sensor assembly or the second sensor assembly includes a fuse disposed along a conductive loop formed between the cartridge and the processor, wherein the fuse is configured to complete the conductive loop prior to the firing stroke, wherein the fuse is configured to disrupt the conductive loop in response to completion of the firing stroke.

Example 11

The surgical stapling instrument of Example 10, further comprising a knife member coupled with the movable member, wherein the knife member is configured to break the fuse during the firing stroke.

Example 12

The surgical stapling instrument of Example 11, wherein the fuse includes a latch, wherein the latch is operable for resetting the fuse after the fuse has been broken during the firing stroke.

Example 13

The surgical stapling instrument of any of the preceding Examples, wherein one of the first sensor assembly or the second sensor assembly includes a hall effect sensor, wherein the movable member includes a magnet, wherein the hall effect sensor is operable to sense a longitudinal position of the movable member based on a longitudinal position of the magnet.

Example 14

The surgical stapling instrument of any of the preceding Examples, wherein one of the first sensor assembly or the second sensor assembly includes an inductive sensor, wherein the movable member includes a metallic portion, wherein the inductive sensor is operable to sense a longitudinal position of the movable member based on a longitudinal position of the metallic portion.

Example 15

The surgical stapling instrument of any of the preceding Examples, wherein one of the first sensor assembly or the second sensor assembly includes an inductive sensor, wherein the inductive sensor is operable to sense at least one of the plurality of staples.

Example 16

A surgical stapling instrument, comprising: (a) a shaft assembly extending along a longitudinal axis to a distal end; (b) an end effector at the distal end of the shaft assembly, wherein the end effector includes: (i) a first jaw having an anvil, and (ii) a second jaw, wherein the first and second jaws are operable to clamp tissue therebetween; (c) a stapling assembly supported by the second jaw of the end effector, wherein the stapling assembly includes: (i) a plurality of staples, and (ii) a movable member translatable distally through the stapling assembly during a firing stroke of the end effector to discharge the plurality of staples into the tissue, and (d) a first processor configured to receive a first electrical signal indicative of a first safety condition of the stapling assembly and a second electrical signal indicative of a second safety condition of the stapling assembly, wherein the first processor is configured to restrict the firing stroke if the first safety condition is unequal to the second safety condition.

Example 17

The surgical stapling instrument of Example 16, wherein the stapling assembly comprises a cartridge insertable into the second jaw, wherein each of the first safety condition and the second safety condition is configured to indicate whether the cartridge is unspent.

Example 18

The surgical stapling instrument of any of Examples 16 through 17, further comprising: (i) a first sensor assembly configured to generate the first electrical signal; and (ii) a second sensor assembly configured to generate the second electrical signal.

Example 19

The surgical stapling instrument of any of Examples 16 through 19, further comprising a second processor configured to receive the first electrical signal and the second electrical signal, wherein the second processor is configured to restrict the firing stroke if the first safety condition is unequal to the second safety condition.

Example 20

The surgical stapling instrument of Example 19, wherein the processor is configured to monitor the first electrical signal and the second electrical signal independently, wherein the processor is configured to restrict the firing stroke based upon at least one of the first electrical signal or the second electrical signal indicating a negative condition of the stapling assembly.

V. Miscellaneous

Any one or more of the teachings, expressions, embodiments, examples, etc. described herein may be combined with any one or more of the teachings, expressions, embodiments, examples, etc. described in U.S. patent application Ser. No. 17/402,674, entitled "Methods of Operating a Robotic Surgical Stapler," filed on Aug. 16, 2021, published as U.S. Pub. No. 2023/0051361 on Feb. 16, 2023; U.S. patent application Ser. No. 17/402,675, entitled "Multi-Threshold Motor Control Algorithm for Powered Surgical Stapler," filed Aug. 16, 2021, published as U.S. Pub. No. 2023/0051271 on Feb. 16, 2023; U.S. patent application Ser. No. 17/402,677, entitled "Variable Response Motor Control Algorithm for Powered Surgical Stapler," filed on Aug. 16, 2021, published as U.S. Pat. No. 11,944,297 on Apr. 2, 2024; U.S. patent application Ser. No. 17/402,679, entitled "Powered Surgical Stapler Having Independently Operable Closure and Firing Systems," filed on Aug. 16, 2021, issued as U.S. Pat. No. 11,779,332 on Oct. 10, 2023; U.S. patent application Ser. No. 17/402,695, entitled "Firing System Features for Surgical Stapler," filed on Aug. 16, 2021, published as U.S. Pub. No. 2023/0050707 on Feb. 16, 2023; U.S. patent application Ser. No. 17/402,703, entitled "Proximally Located Firing Lockout Mechanism for Surgical Stapler," filed on Aug. 16, 2021, published as U.S. Pub. No. 2023/0051105 on Feb. 16, 2023; U.S. patent application Ser. No.17/402,720, entitled "Cartridge-Based Firing Lockout Mechanism for Surgical Stapler," filed on Aug. 16, 2021, published as U.S. Pub. No. 2023/0051222 on Feb. 16, 2023; U.S. patent application Ser. No.17/403,732, entitled "Multi-Position Restraining Member for Sled Movement," filed on Aug. 16, 2021, published as U.S. Pub. No. 2023/0045894 on Feb. 16, 2023; U.S. patent application Ser. No. 17/402,738, entitled "Firing Member Tracking Feature for Surgical Stapler," filed on Aug. 16, 2021, published as U.S. Pub. No. 2023/0049736 on Feb. 16, 2023; U.S. patent application Ser. No. 17/402,744, entitled "Adjustable Power Transmission Mechanism for Powered Surgical Stapler," filed on Aug. 16, 2021, published as U.S. Pub. No. 2023/0051938 on Feb. 16, 2023; U.S. patent application Ser. No. 17/402,749, entitled "Firing Bailout System for Powered Surgical Stapler," filed on Aug. 16, 2021, published as U.S. Pub. No. 2023/0045998 on Feb. 16, 2023; U.S. patent application Ser. No. 17/402, 759; and/or U.S. Pat. App. No., entitled "Deflectable Firing Member for Surgical Stapler," filed on Aug. 16, 2021, published as U.S. Pub. No. 2023/0052307 on Feb. 16, 2023. The disclosure of each of these applications is incorporated by reference herein in its entirety.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the systems, instruments, and/or portions thereof, followed by cleaning or replacement of particular pieces, and subsequent reassembly. In particular, some versions of the systems, instruments, and/or portions thereof may be disassembled, and any number of the particular pieces or parts of the systems, instruments, and/or portions thereof may be selectively replaced or removed in any combination. Upon cleaning and/or replacement of particular parts, some versions of the systems, instruments, and/or portions thereof may be reassembled for subsequent use either at a reconditioning facility, or by an operator immediately prior to a procedure. Those skilled in the art will appreciate that reconditioning of systems, instruments, and/or portions thereof may utilize a variety of techniques for disassembly, cleaning/replacement, and reassembly. Use of such techniques, and the resulting reconditioned systems, instruments, and/or portions thereof, are all within the scope of the present application.

By way of example only, versions described herein may be sterilized before and/or after a procedure. In one sterilization technique, the systems, instruments, and/or portions thereof is placed in a closed and sealed container, such as a plastic or TYVEK bag. The container and system, instrument, and/or portion thereof may then be placed in a field of radiation that can penetrate the container, such as gamma radiation, x-rays, or high-energy electrons. The radiation may kill bacteria on the system, instrument, and/or portion thereof and in the container. The sterilized systems, instruments, and/or portions thereof may then be stored in the sterile container for later use. Systems, instruments, and/or portions thereof may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been men-

We claim:
1. A surgical stapling instrument, comprising:
(a) a shaft assembly extending along a longitudinal axis to a distal end;
(b) an end effector at the distal end of the shaft assembly, wherein the end effector includes:
(i) a first jaw having an anvil, and
(ii) a second jaw, wherein the first and second jaws are operable to clamp tissue therebetween;
(c) a cartridge insertable into the second jaw of the end effector, wherein the cartridge includes:
(i) a plurality of staples,
(ii) a movable member translatable distally through the cartridge during a firing stroke of the end effector to discharge the plurality of staples into the tissue,
(iii) a first sensor assembly configured to monitor a first condition of the cartridge when the cartridge is inserted into the second jaw of the end effector, and
(iv) a second sensor assembly configured to monitor a second condition of the cartridge when the cartridge is inserted into the second jaw of the end effector; and
(d) a first processor coupled with the first sensor assembly and the second sensor assembly, wherein the first processor is configured to receive a first signal from the first sensor assembly indicative of the first condition of the cartridge and a second signal from the second sensor assembly indicative of the second condition of the cartridge, wherein the first processor is configured to selectively permit or restrict the firing stroke based upon the first signal and the second signal,
wherein one of the first sensor assembly or the second sensor assembly includes a first RFID power coil and an RFID tag, wherein the first RFID power coil is disposed on the second jaw of the end effector and the RFID tag is disposed on the movable member, wherein the first RFID power coil is operable to read a set of cartridge information from the RFID tag.

2. The surgical stapling instrument of claim 1, wherein the first processor is configured to monitor the first signal and the second signal independently, wherein the first processor is configured to restrict the firing stroke based upon either the first signal or the second signal indicating a negative condition of the cartridge.

3. The surgical stapling instrument of claim 2, wherein the negative condition of the cartridge includes at least one of a first negative condition, a second negative condition, or a third negative condition, wherein the first negative condition is indicative of the cartridge being improperly inserted into the second jaw of the end effector, wherein the second negative condition is indicative of the cartridge being spent, wherein the third negative condition is indicative of the cartridge being incompatible with the end effector.

4. The surgical stapling instrument of claim 1, wherein the first condition of the cartridge and the second condition of the cartridge are the same.

5. The surgical stapling instrument of claim 1, wherein the first condition of the cartridge and the second condition of the cartridge are different.

6. The surgical stapling instrument of claim 1, further comprising a second processor coupled with the first sensor assembly and the second sensor assembly, wherein the second processor is configured to receive the first signal from the first sensor assembly indicative of the first condition of the cartridge and the second signal from the second sensor assembly indicative of the second condition of the cartridge, wherein the second processor is configured to selectively permit or restrict the firing stroke based upon the first signal and the second signal.

7. The surgical stapling instrument of claim 1, wherein the one of the first sensor assembly or the second sensor assembly includes a second RFID power coil, wherein the first RFID power coil is disposed at a proximal position of the second jaw, wherein the second RFID power coil is disposed at a distal position of the second jaw.

8. The surgical stapling instrument of claim 7, wherein the second RFID power coil is operable to write to the RFID tag, wherein upon the completion of the firing stroke the second RFID power coil is configured to write to the RFID tag.

9. The surgical stapling instrument of claim 1, wherein one of the first sensor assembly or the second sensor assembly includes a fuse disposed along a conductive loop formed between the cartridge and the first processor, wherein the fuse is configured to complete the conductive loop prior to the firing stroke, wherein the fuse is configured to disrupt the conductive loop in response to completion of the firing stroke.

10. The surgical stapling instrument of claim 9, further comprising a knife member coupled with the movable member, wherein the knife member is configured to break the fuse during the firing stroke.

11. The surgical stapling instrument of claim 10, wherein the fuse includes a latch, wherein the latch is operable for resetting the fuse after the fuse has been broken during the firing stroke.

12. The surgical stapling instrument of claim 1, wherein one of the first sensor assembly or the second sensor assembly includes a hall effect sensor, wherein the movable member includes a magnet, wherein the hall effect sensor is operable to sense a longitudinal position of the movable member based on a longitudinal position of the magnet.

13. The surgical stapling instrument of claim 1, wherein one of the first sensor assembly or the second sensor assembly includes an inductive sensor, wherein the movable member includes a metallic portion, wherein the inductive sensor is operable to sense a longitudinal position of the movable member based on a longitudinal position of the metallic portion.

14. The surgical stapling instrument of claim 1, wherein one of the first sensor assembly or the second sensor assembly includes an inductive sensor, wherein the inductive sensor is operable to sense at least one of the plurality of staples.

15. A surgical stapling instrument, comprising:
(a) a shaft assembly extending along a longitudinal axis to a distal end;
(b) an end effector at the distal end of the shaft assembly, wherein the end effector includes:
(i) a first jaw having an anvil, and
(ii) a second jaw, wherein the first and second jaws are operable to clamp tissue therebetween;
(c) a stapling assembly supported by the second jaw of the end effector, wherein the stapling assembly includes:
(i) a plurality of staples, and (ii) a movable member translatable distally through the stapling assembly during a firing stroke of the end effector to discharge the plurality of staples into the tissue;

(d) a first processor configured to receive a first electrical signal indicative of a first safety condition of the stapling assembly and a second electrical signal indicative of a second safety condition of the stapling assembly, wherein the first processor is configured to restrict the firing stroke if the first safety condition is unequal to the second safety condition; and (e) a second processor configured to receive the first electrical signal and the second electrical signal, wherein the second processor is configured to restrict the firing stroke if the first safety condition is unequal to the second safety condition.

16. The surgical stapling instrument of claim 15, wherein the stapling assembly comprises a cartridge insertable into the second jaw, wherein each of the first safety condition and the second safety condition is configured to indicate whether the cartridge is unspent.

17. The surgical stapling instrument of claim 16, further comprising:
(i) a first sensor assembly configured to generate the first electrical signal; and
(ii) a second sensor assembly configured to generate the second electrical signal.

18. A surgical stapling instrument, comprising:
(a) a shaft assembly extending along a longitudinal axis to a distal end;
(b) an end effector at the distal end of the shaft assembly, wherein the end effector includes:
(i) a first jaw having an anvil, and
(ii) a second jaw, wherein the first and second jaws are operable to clamp tissue therebetween;
(c) a stapling assembly supported by the second jaw of the end effector, wherein the stapling assembly includes:
(i) a plurality of staples,
(ii) a movable member translatable distally through the stapling assembly during a firing stroke of the end effector to discharge the plurality of staples into the tissue;
(d) a processor configured to receive a first electrical signal indicative of a first safety condition of the stapling assembly and a second electrical signal indicative of a second safety condition of the stapling assembly;
(e) a first sensor assembly configured to generate the first electrical signal; and
(f) a second sensor assembly configured to generate the second electrical signal,
wherein the processor is configured to monitor the first electrical signal and the second electrical signal independently, wherein the processor is configured to restrict the firing stroke based upon at least one of the first electrical signal or the second electrical signal indicating a negative condition of the stapling assembly,
wherein one of the first sensor assembly or the second sensor assembly includes a fuse disposed along a conductive loop formed between the stapling assembly and the processor, wherein the fuse is configured to complete the conductive loop prior to the firing stroke, wherein the fuse is configured to disrupt the conductive loop in response to completion of the firing stroke.

* * * * *